US008870827B2

(12) United States Patent
Young et al.

(10) Patent No.: US 8,870,827 B2
(45) Date of Patent: *Oct. 28, 2014

(54) AUTOMATIC INJECTOR

(75) Inventors: Matthew Egerton Young, Over Cambs (GB); Sophie Rebecca Raven, Swavesey Cambs (GB); Christopher John Hurlstone, Newport Saffron Walden (GB); Craig Malcolm Rochford, Monxton Andover Hants (GB); Colin James Mathews, Godmanchester Huntingdon (GB); Robert L. Hill, Abingdon, MD (US); John Glyndwr Wilmot, Mount Airy, MD (US)

(73) Assignee: Meridian Medical Technologies, Inc., Columbia, MD (US)

( * ) Notice: Subject to any disclaimer, the term of this patent is extended or adjusted under 35 U.S.C. 154(b) by 419 days.

This patent is subject to a terminal disclaimer.

(21) Appl. No.: 12/857,641

(22) Filed: Aug. 17, 2010

(65) Prior Publication Data

US 2010/0318037 A1 Dec. 16, 2010

Related U.S. Application Data

(63) Continuation of application No. 11/923,729, filed on Oct. 25, 2007, now Pat. No. 7,794,432, which is a continuation of application No. 11/095,664, filed on Apr. 1, 2005, now Pat. No. 7,449,012.

(60) Provisional application No. 60/599,054, filed on Aug. 6, 2004.

(51) Int. Cl.
| | |
|---|---|
| A61M 5/20 | (2006.01) |
| A61M 5/32 | (2006.01) |
| A61M 5/24 | (2006.01) |
| A61M 5/31 | (2006.01) |

(52) U.S. Cl.
CPC ..... *A61M 5/2033* (2013.01); *A61M 2005/2013* (2013.01); *A61M 2005/3247* (2013.01); *A61M 5/2459* (2013.01); *A61M 5/3271* (2013.01); *A61M 5/3129* (2013.01); *A61M 2005/2073* (2013.01); *A61M 5/326* (2013.01); *A61M 2005/206* (2013.01)
USPC .......................................... 604/192; 604/198

(58) Field of Classification Search
USPC .......................................... 604/187, 192, 198
See application file for complete search history.

(56) References Cited

U.S. PATENT DOCUMENTS

| | | |
|---|---|---|
| 2,866,458 A | 12/1958 | Hein |
| 3,882,863 A | 5/1975 | Sarnoff et al. |

(Continued)

FOREIGN PATENT DOCUMENTS

| | | |
|---|---|---|
| DE | 198 21 933 C1 | 11/1999 |
| EP | 0 824 923 A1 | 2/1998 |

(Continued)

OTHER PUBLICATIONS

Defendant Intelliject's Answer. Affirmative Defenses, and Counterclaims dated Feb. 11, 2011 submitted in *King Pharm., Inc* v. *Intelliject, Inc.*, pp. 16-47, Civil Action No. 11-065 (BMS), U.S. District Court for the District of Delaware.

*Primary Examiner* — Kevin C Sirmons
*Assistant Examiner* — Deanna K Hall
(74) *Attorney, Agent, or Firm* — Stephanie J. Monaco

(57) ABSTRACT

An automatic injector dispenses a predetermined dose of medicament without a user having to manually force the needle into an injection site. The automatic injector includes a needle cover having a locked retracted position with respect to the injector housing prior to a medicament dispensing operation. The needle cover is operative to engage an injection site prior to a medicament dispensing operation.

25 Claims, 26 Drawing Sheets

(56) References Cited

U.S. PATENT DOCUMENTS

| | | | |
|---|---|---|---|
| 4,031,893 A | 6/1977 | Kaplan et al. |
| 4,226,235 A | 10/1980 | Sarnoff et al. |
| 4,329,988 A | 5/1982 | Sarnoff et al. |
| 4,394,863 A | 7/1983 | Bartner |
| 4,723,937 A | 2/1988 | Sarnoff et al. |
| 5,026,349 A | 6/1991 | Schmitz et al. |
| 5,282,793 A | 2/1994 | Larson |
| 5,295,965 A | 3/1994 | Wilmot |
| 5,405,362 A | 4/1995 | Kramer et al. |
| 5,478,316 A | 12/1995 | Bitdinger et al. |
| 5,599,309 A | 2/1997 | Marshall et al. |
| 5,658,259 A | 8/1997 | Pearson et al. |
| 5,713,866 A | 2/1998 | Wilmot |
| 5,776,107 A | 7/1998 | Cherif-Cheikh |
| 5,957,897 A | 9/1999 | Jeffrey |
| 6,210,369 B1 | 4/2001 | Wilmot et al. |
| 6,258,068 B1 | 7/2001 | Kirchofer et al. |
| 6,280,421 B1 | 8/2001 | Kirchofer et al. |
| 6,391,003 B1 | 5/2002 | Lesch, Jr. |
| 6,428,528 B2 | 8/2002 | Sadowski et al. |
| 6,544,234 B1 | 4/2003 | Gabriel |
| 6,565,553 B2 | 5/2003 | Sadowski et al. |
| 6,641,561 B1 | 11/2003 | Hill et al. |
| 6,689,092 B2 | 2/2004 | Zierenberg et al. |
| 6,746,429 B2 | 6/2004 | Sadowski et al. |
| 6,767,336 B1 | 7/2004 | Kaplan |
| 6,805,686 B1 | 10/2004 | Fathallah et al. |
| 6,846,302 B2 | 1/2005 | Shemesh et al. |
| 6,918,889 B1 | 7/2005 | Brunel |
| 7,104,969 B2 | 9/2006 | Du Plessis |
| 7,488,308 B2 | 2/2009 | Lesch, Jr. |
| 2005/0020979 A1 * | 1/2005 | Westbye et al. ............... 604/151 |
| 2005/0165360 A1 | 7/2005 | Stamp |
| 2006/0270986 A1 | 11/2006 | Hommann et al. |
| 2008/0051715 A1 | 2/2008 | Young et al. |

FOREIGN PATENT DOCUMENTS

| | | |
|---|---|---|
| EP | 0 956 873 A2 | 11/1999 |
| FR | 2 794 650 A1 | 12/2000 |
| WO | WO 91/11212 A1 | 8/1991 |
| WO | WO 97/14455 A1 | 4/1997 |
| WO | WO 99/37343 A1 | 7/1999 |
| WO | WO 01/37898 A2 | 5/2001 |
| WO | WO 02/47746 A1 | 6/2002 |
| WO | WO 02/083211 A1 | 10/2002 |
| WO | WO 03/011378 A1 | 2/2003 |
| WO | WO 03/082386 A1 | 10/2003 |
| WO | WO 2004/108194 A1 | 12/2004 |
| WO | WO 2005/060854 A1 | 7/2005 |
| WO | WO 2005/097238 A1 | 10/2005 |

\* cited by examiner

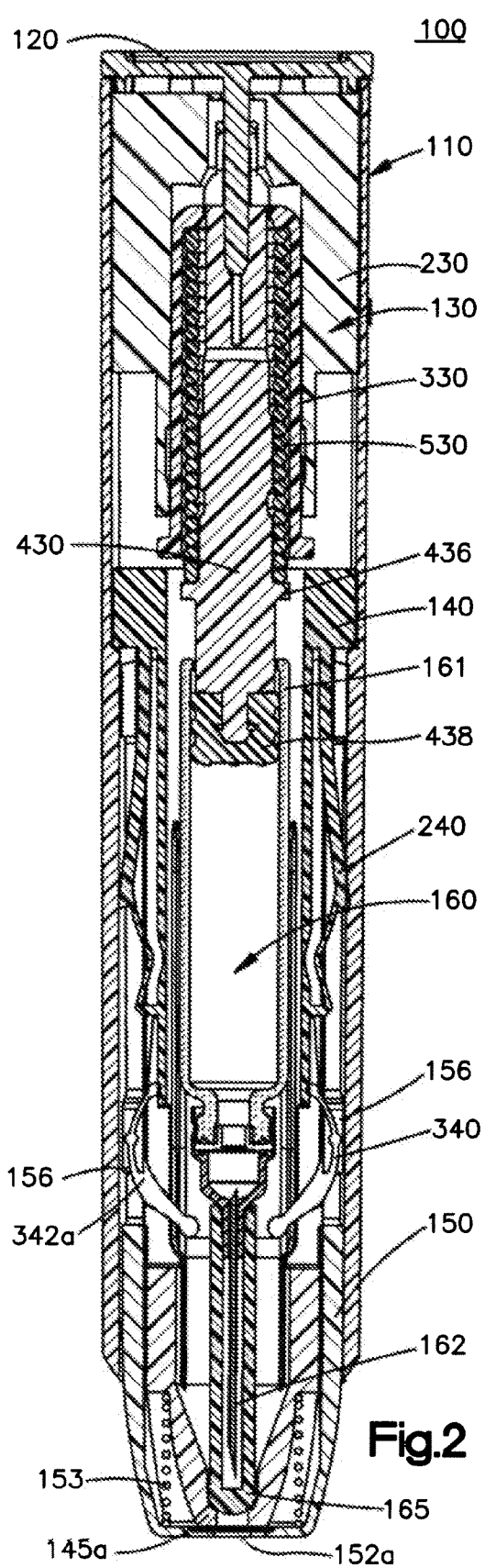
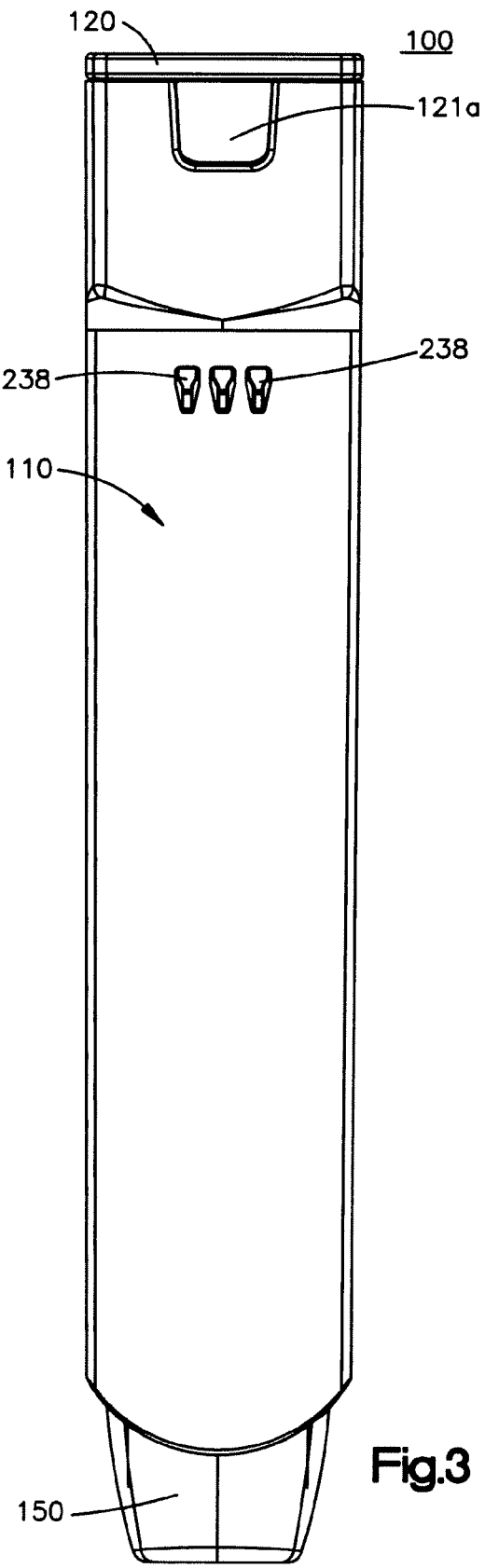
Fig.2
Fig.3

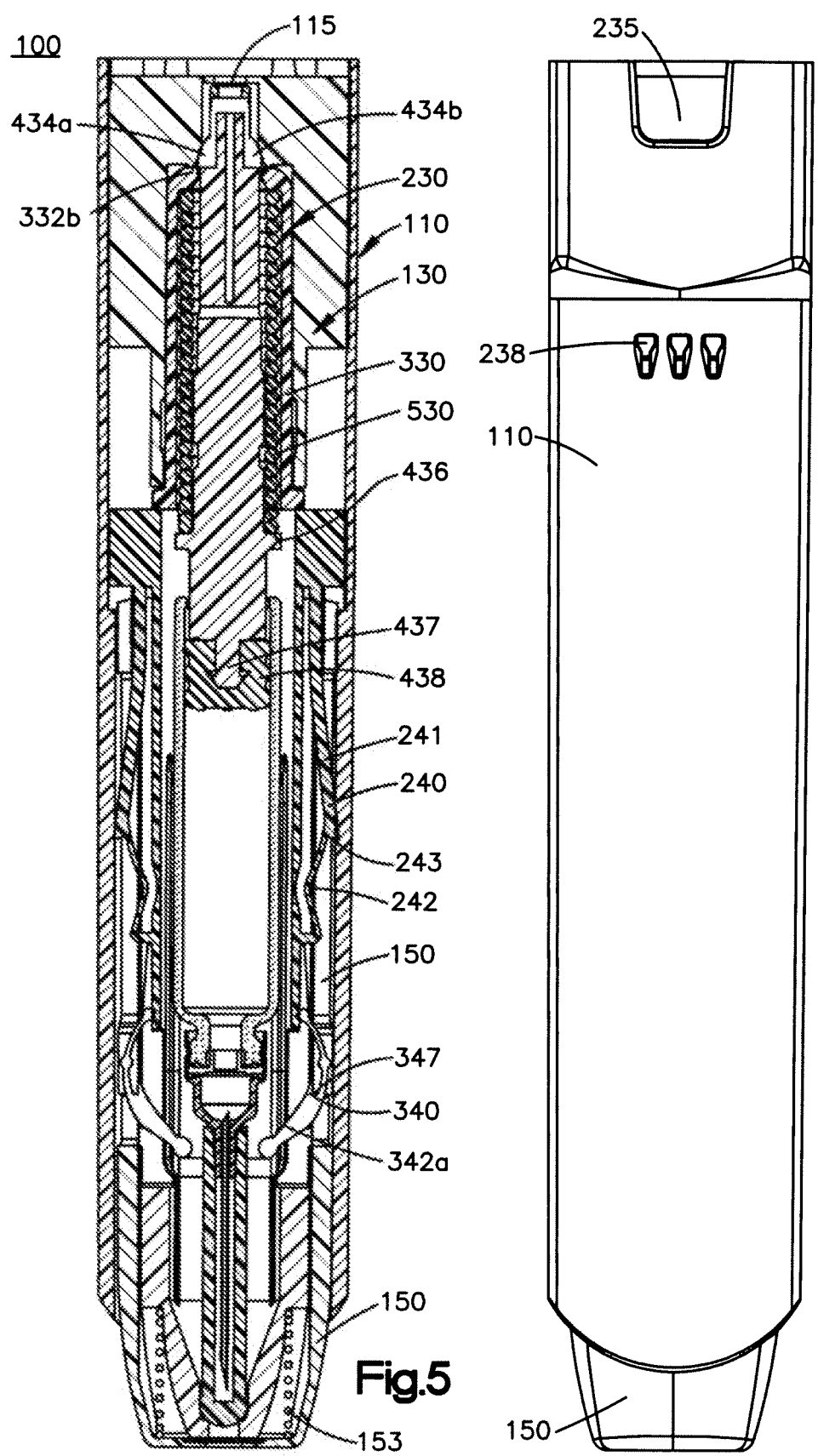

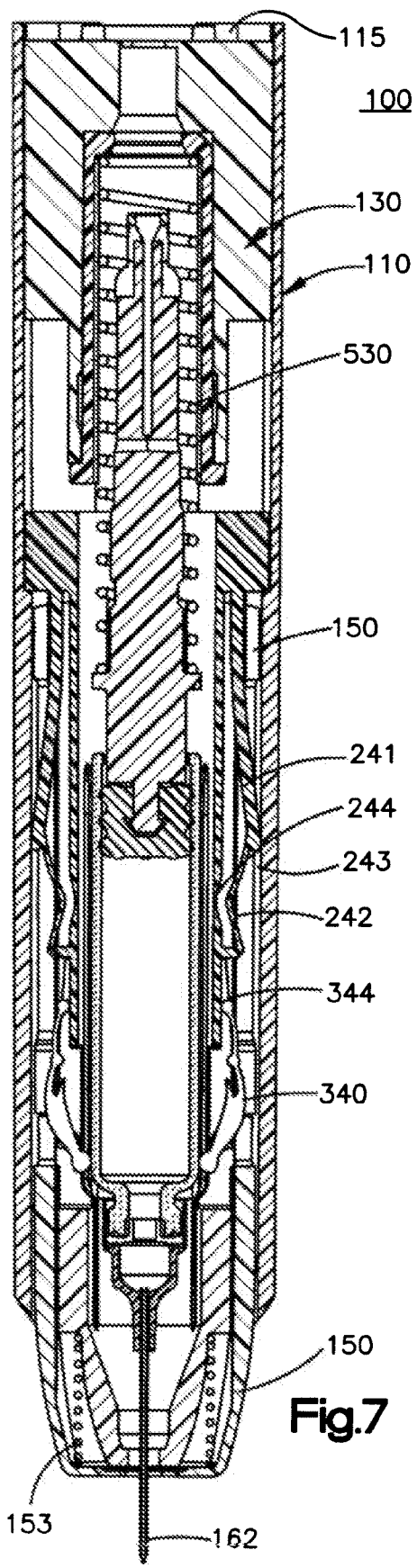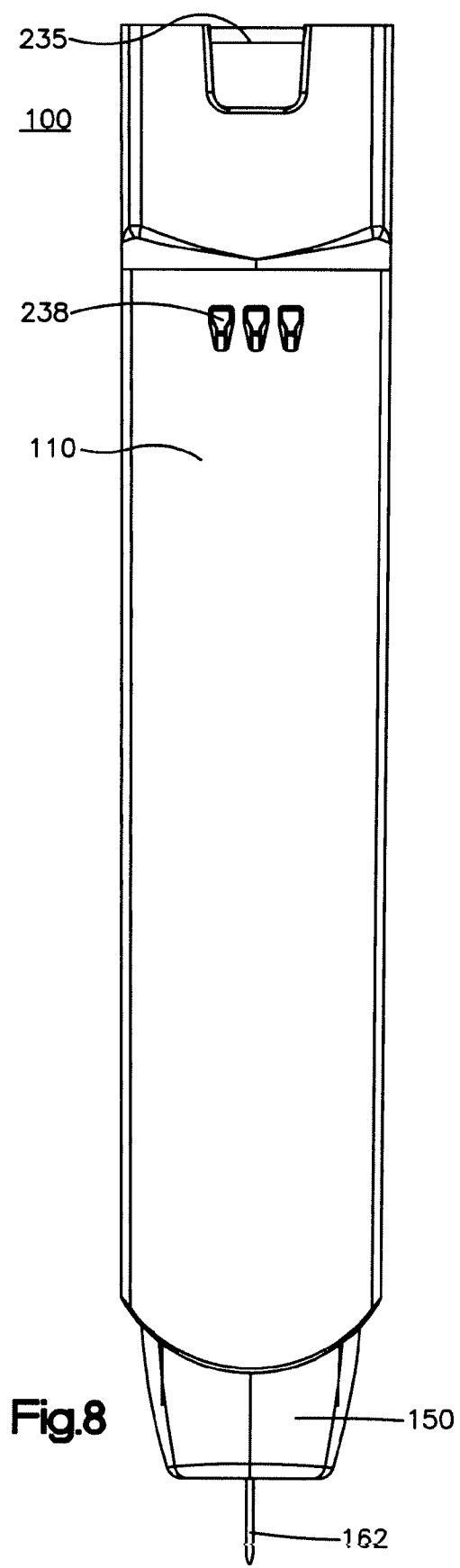

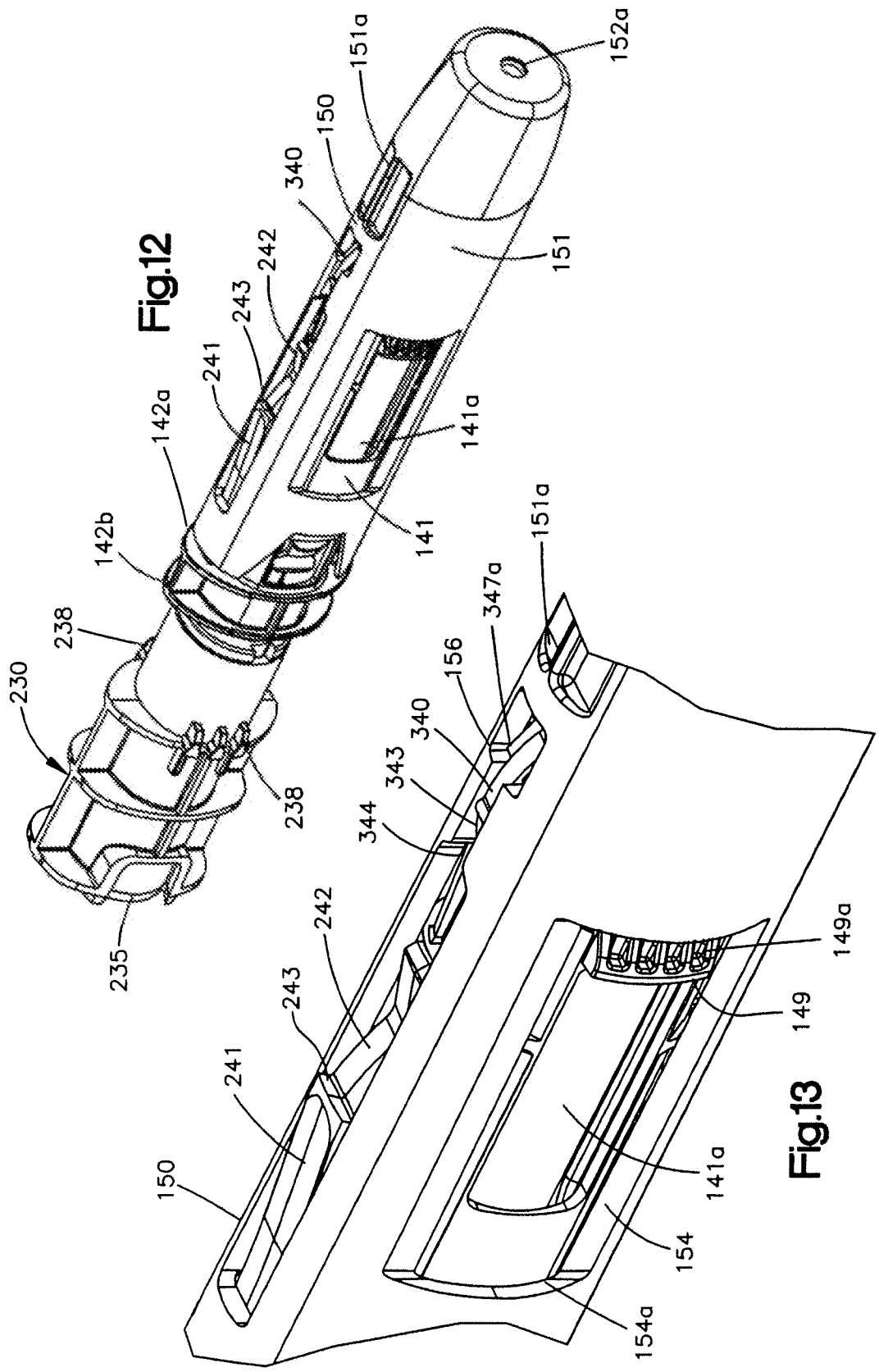

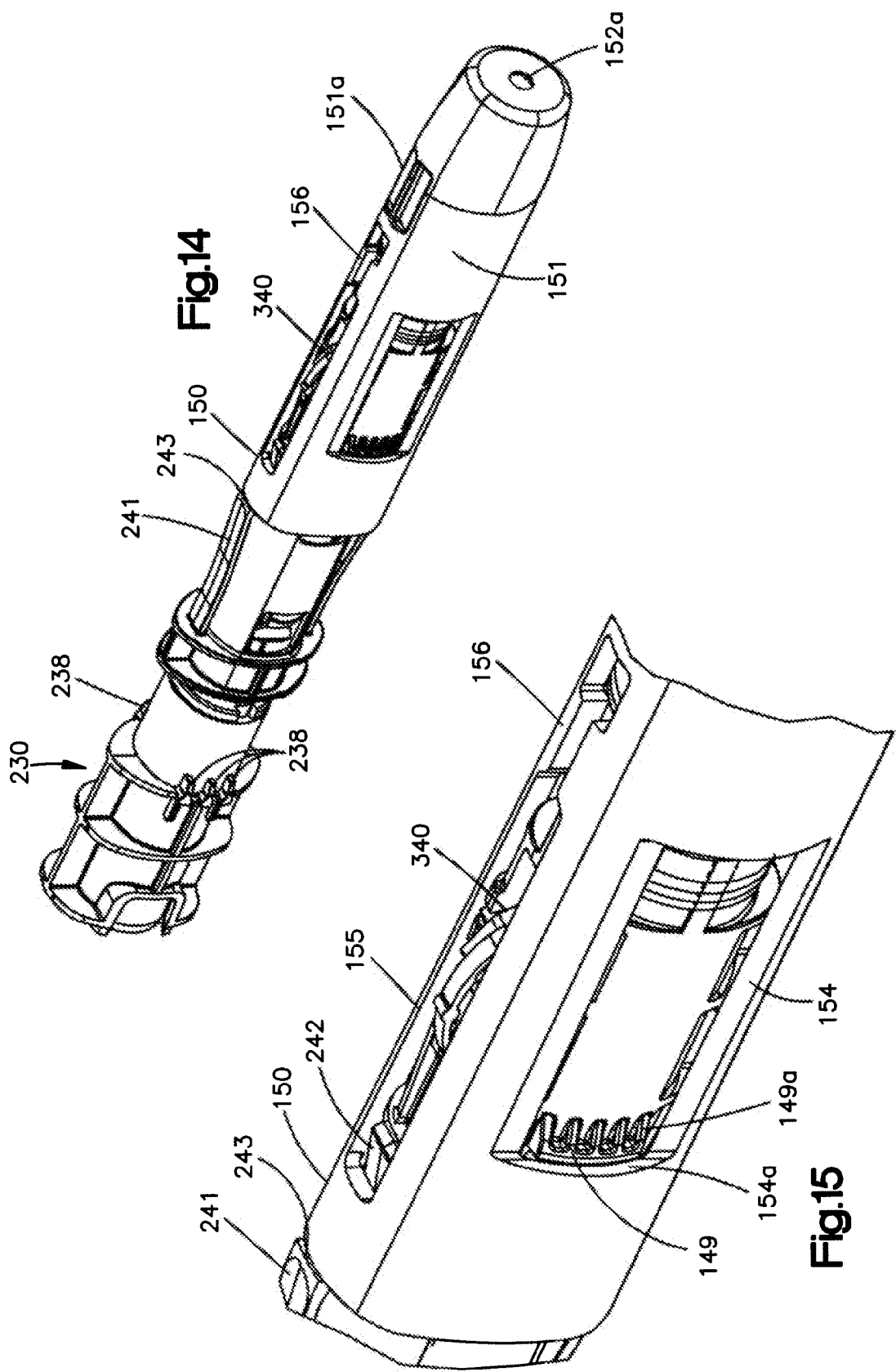

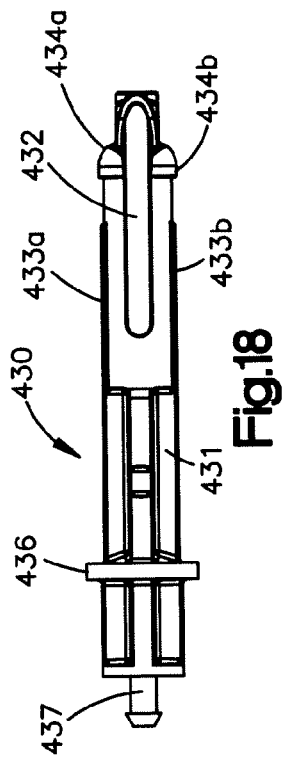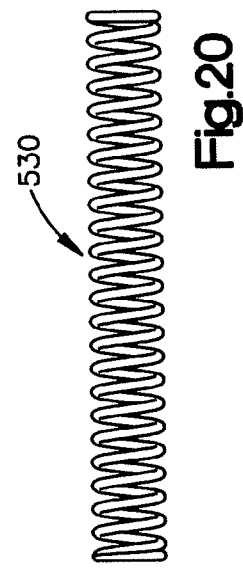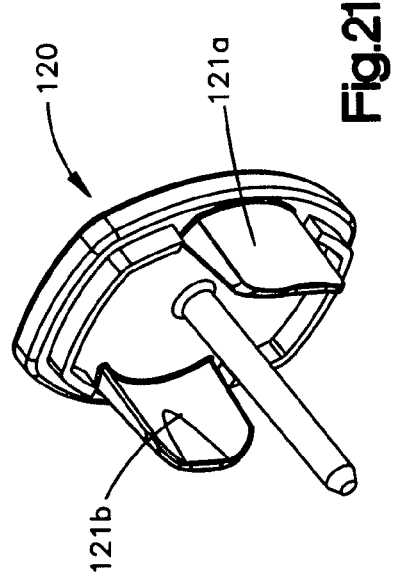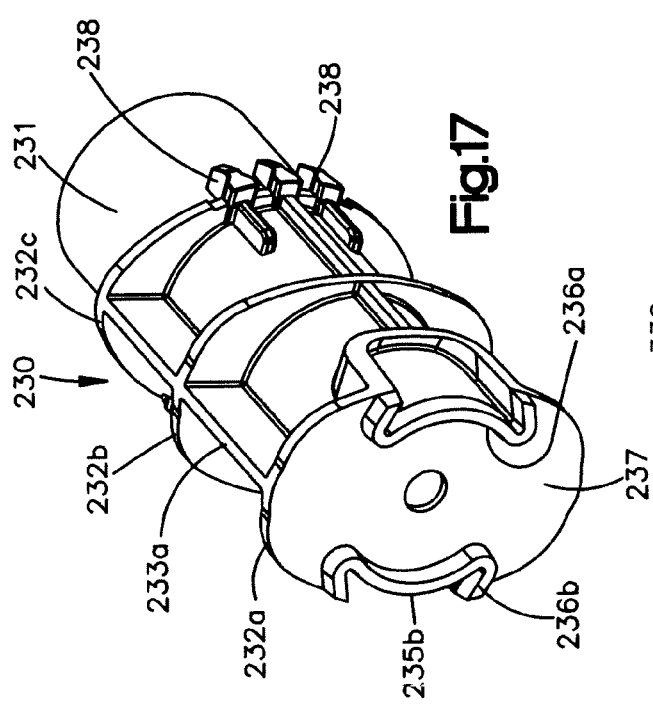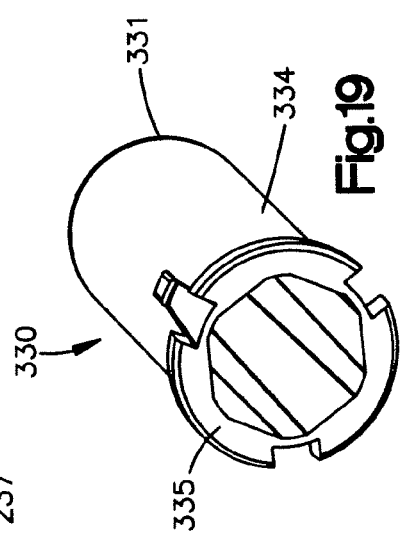

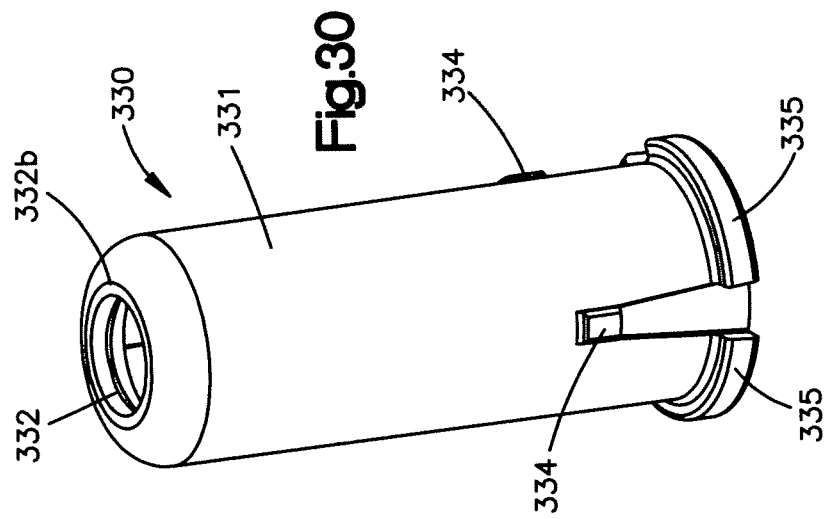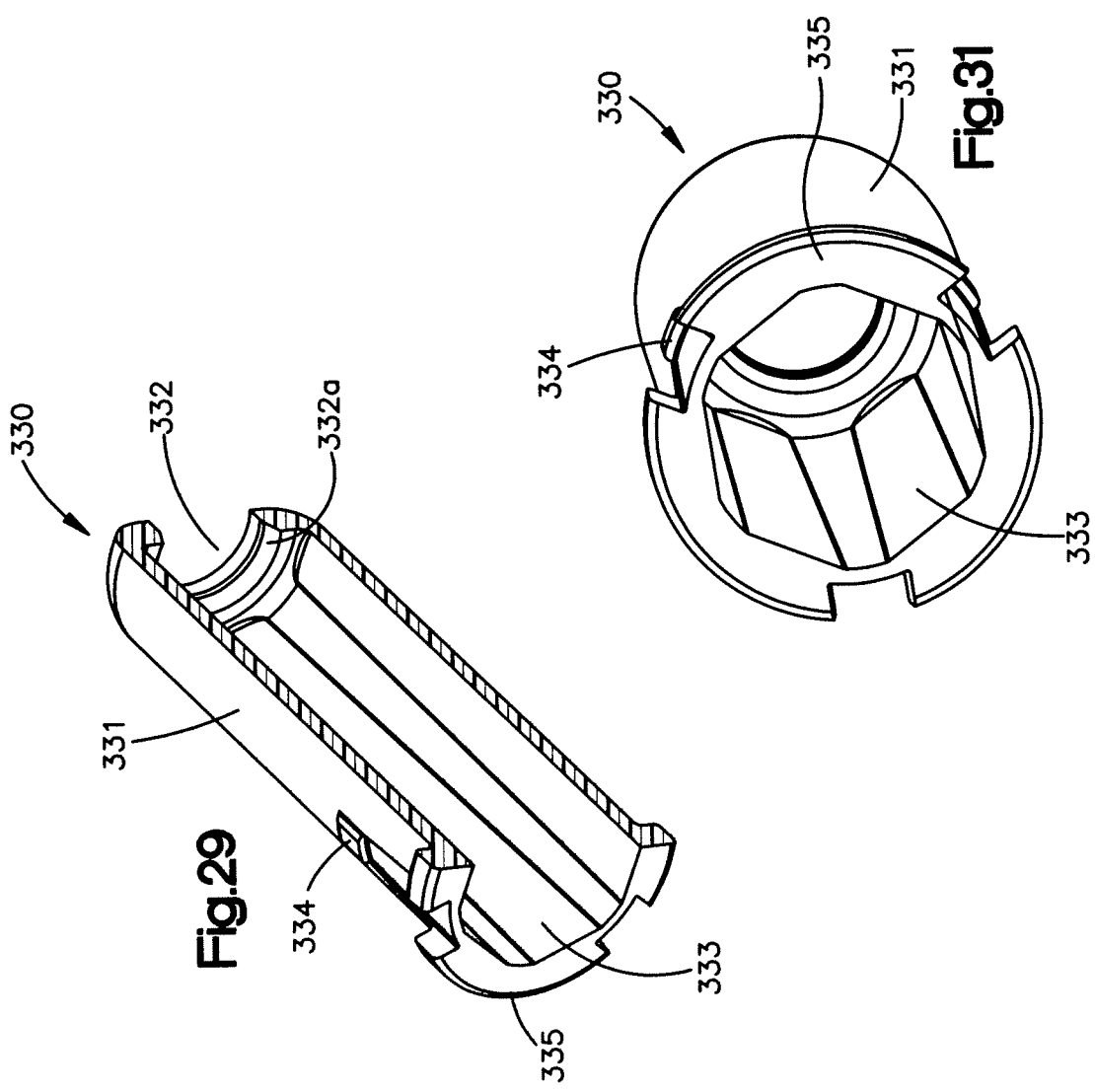

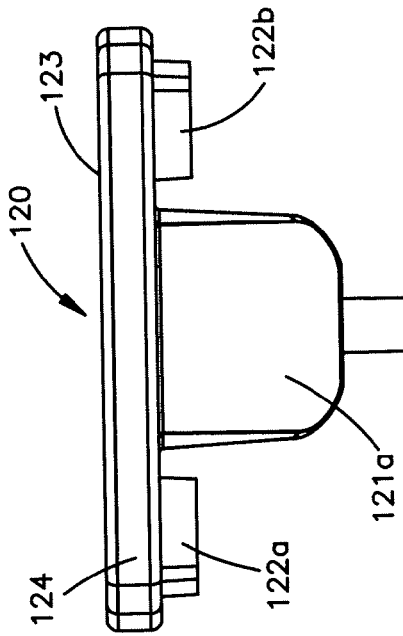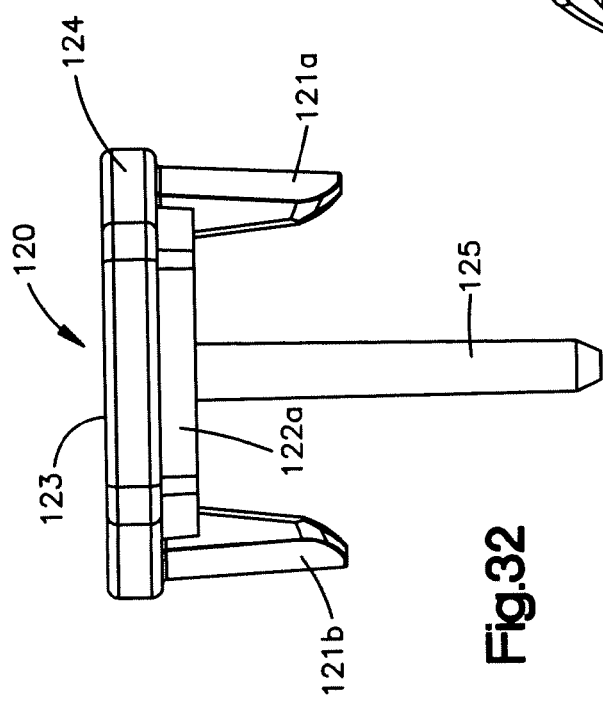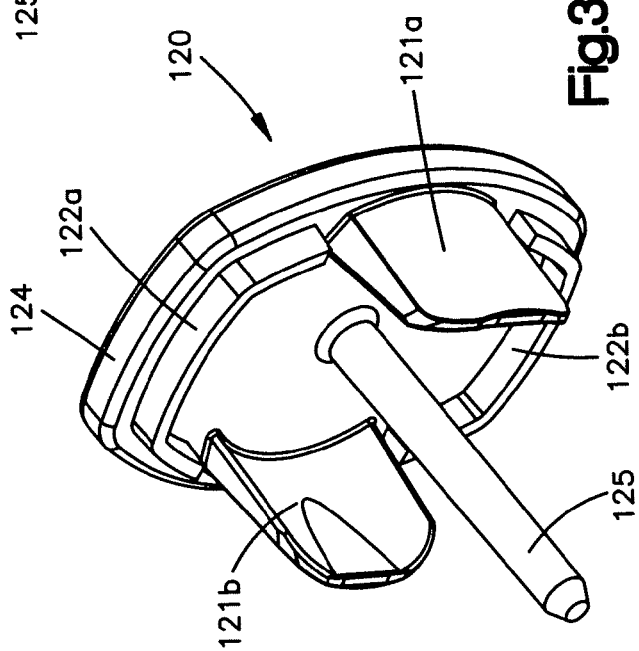

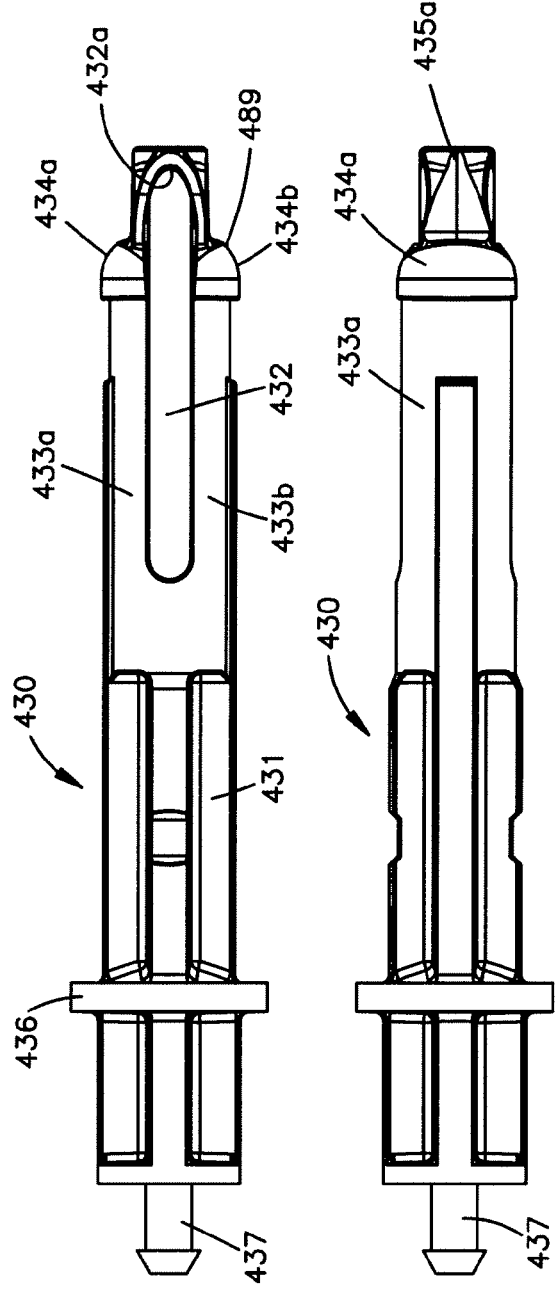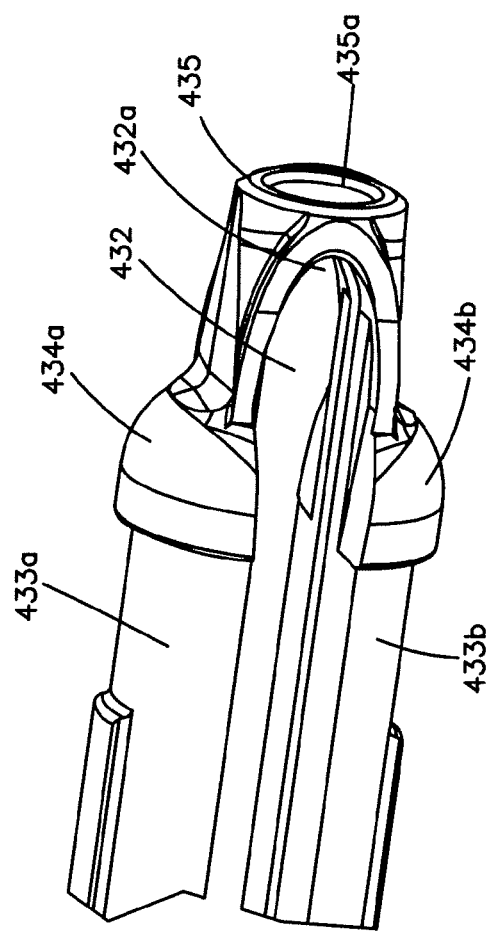
Fig.35  Fig.36  Fig.37

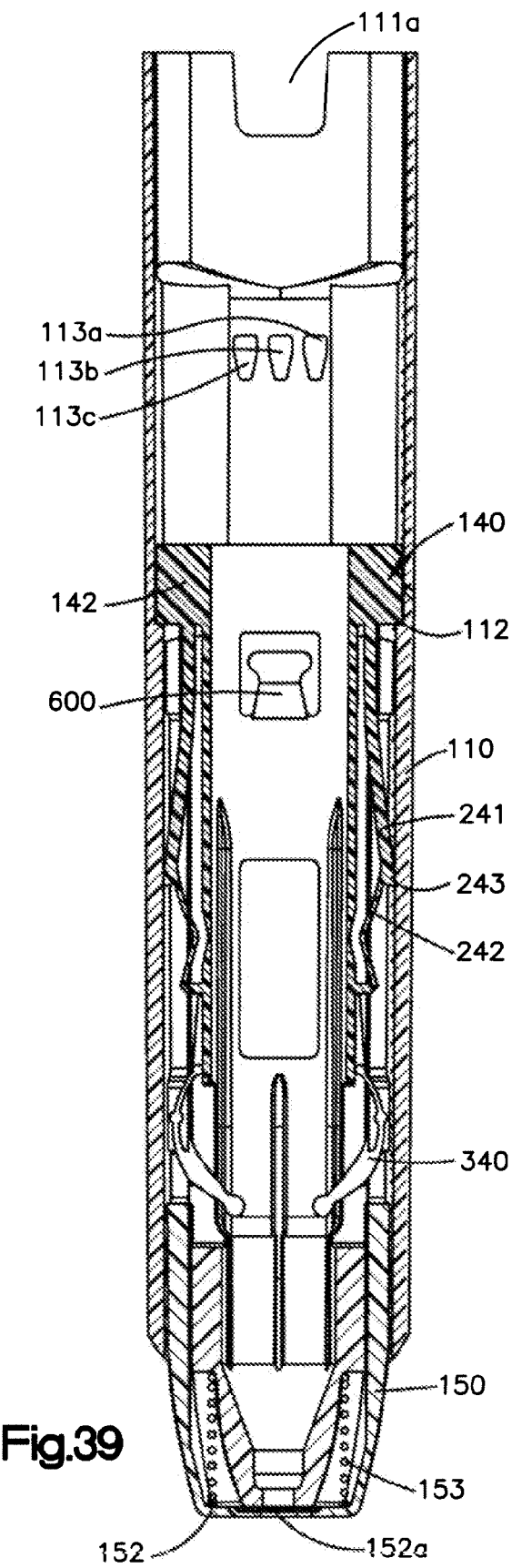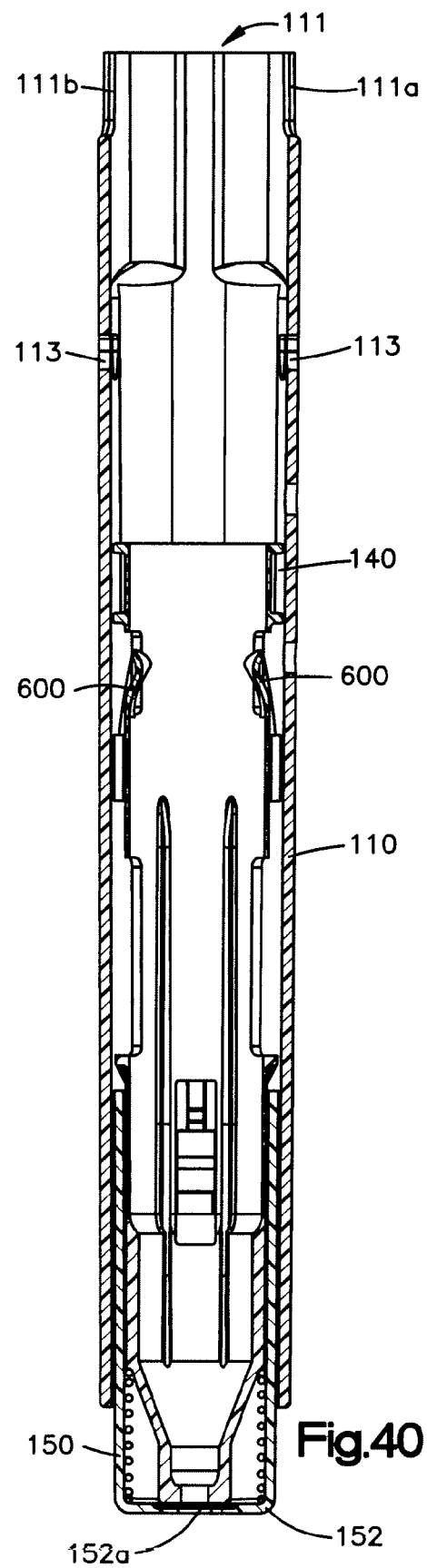

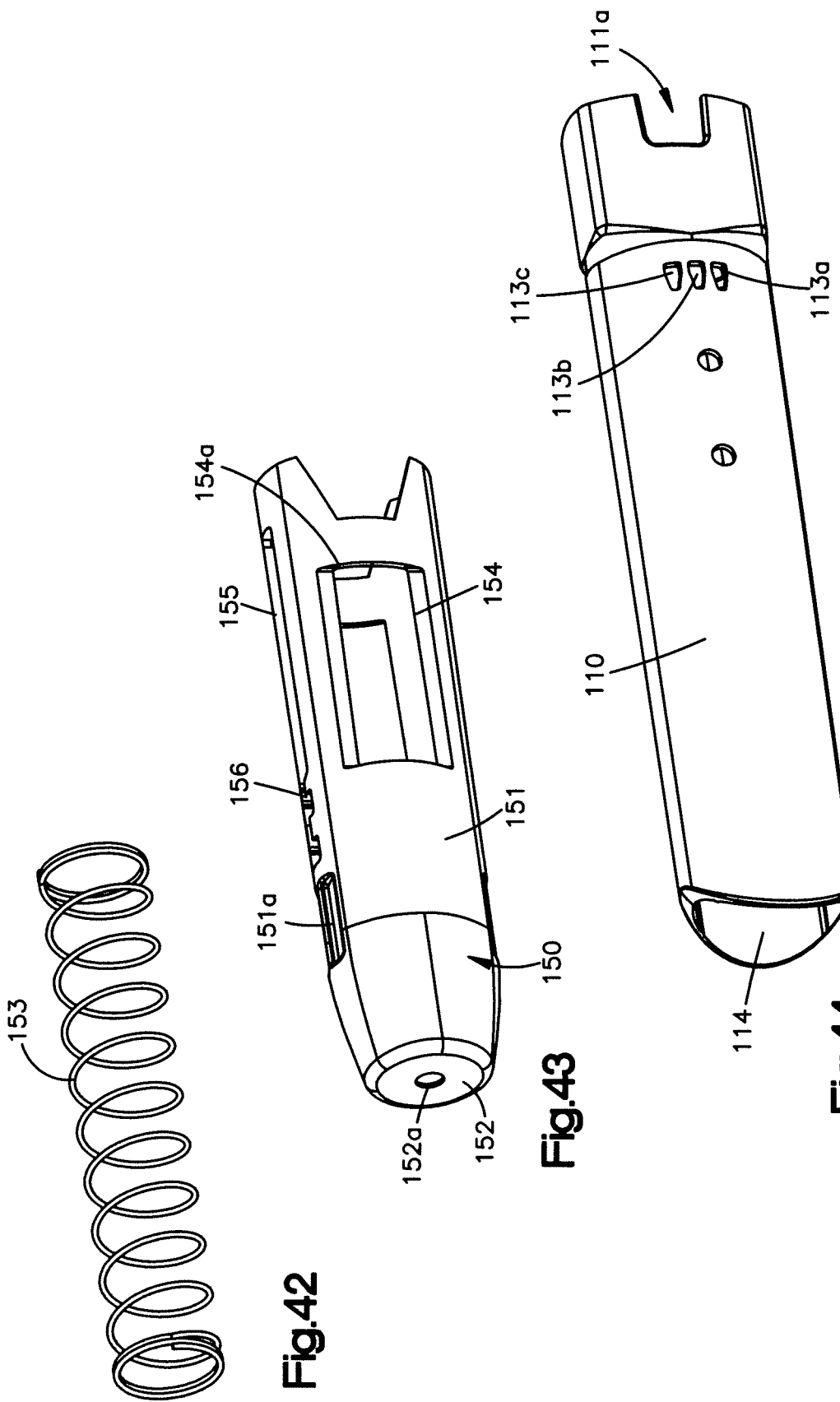

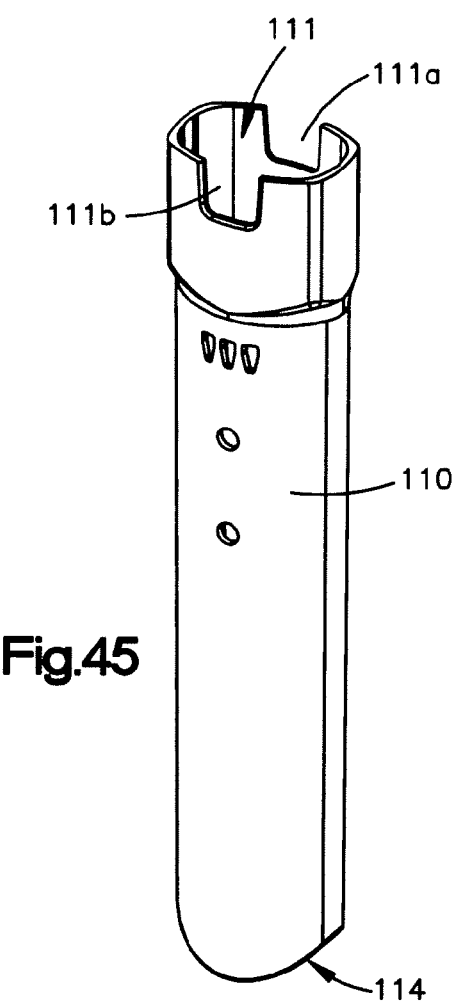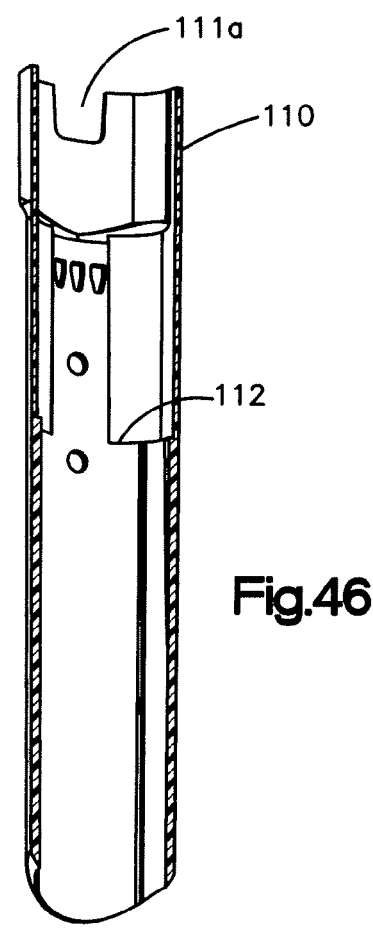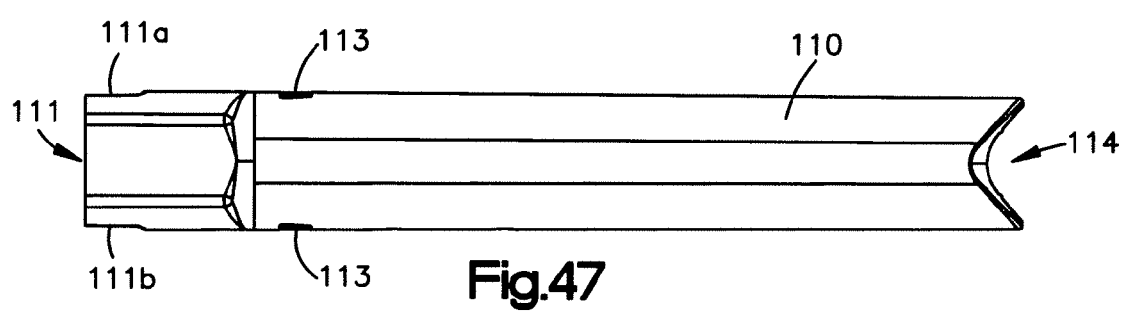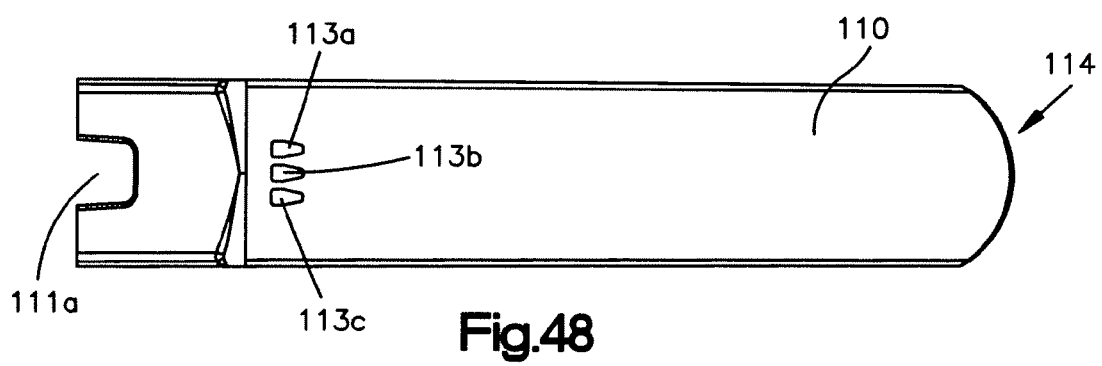

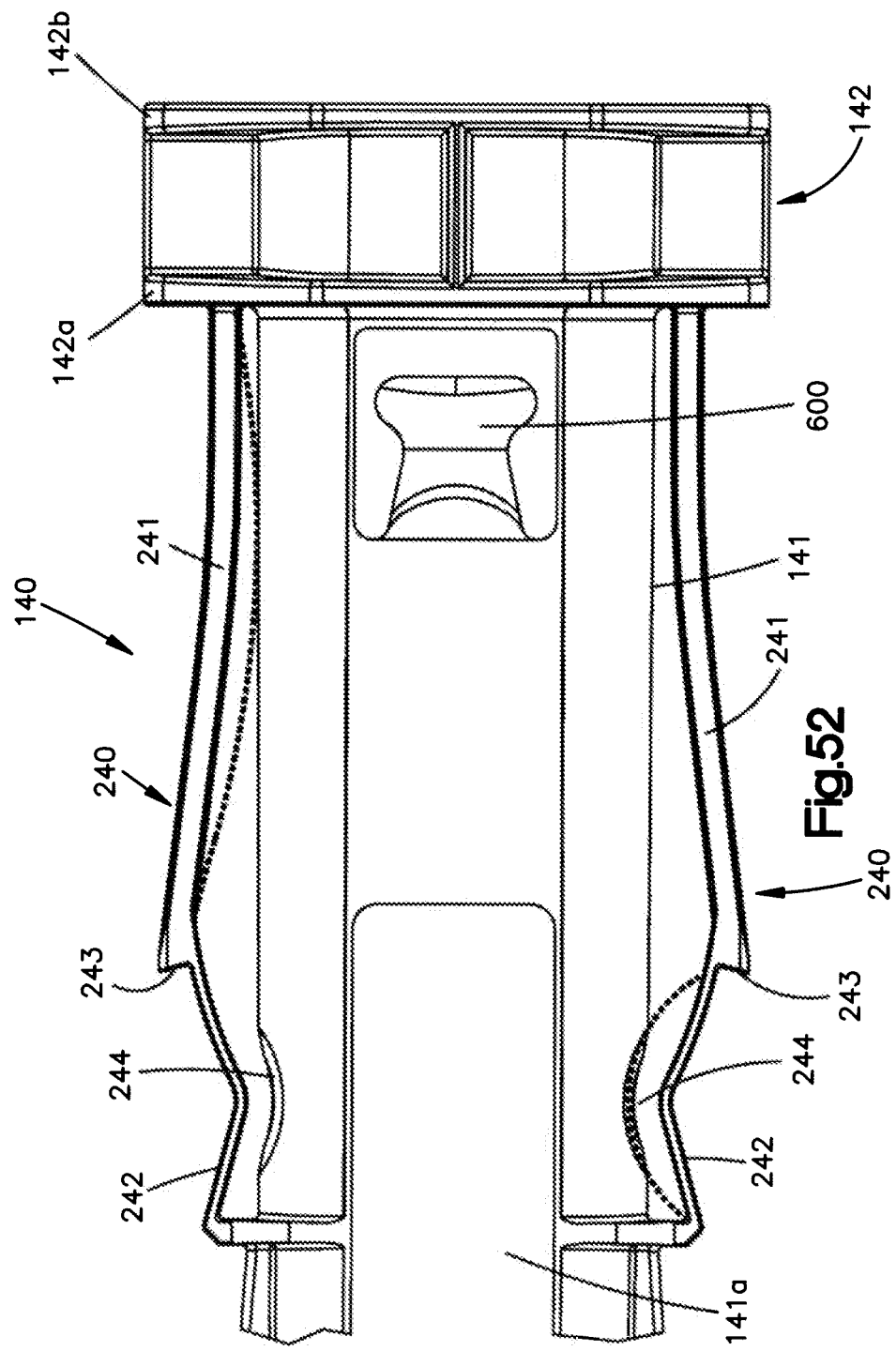

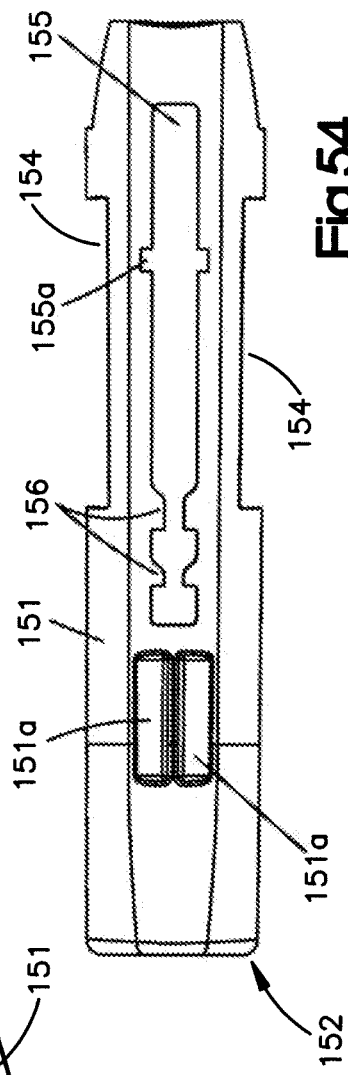
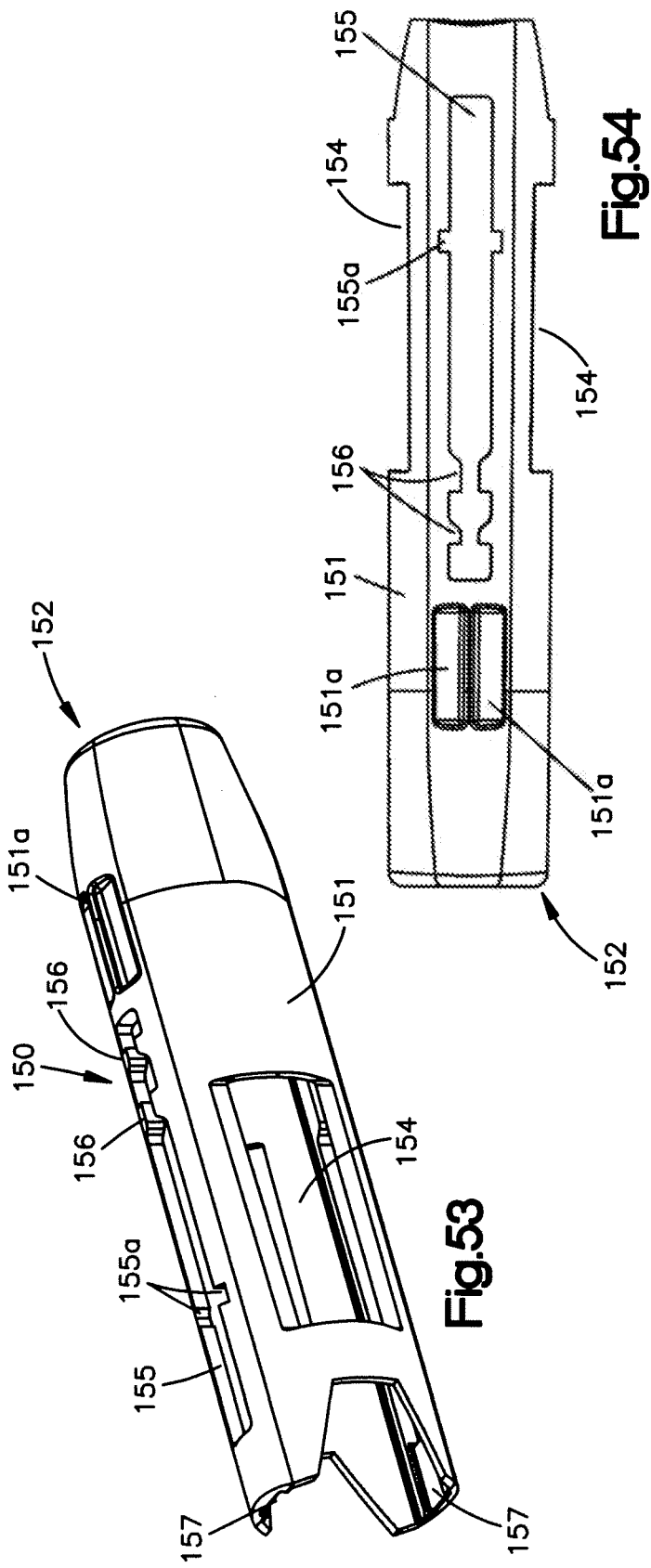
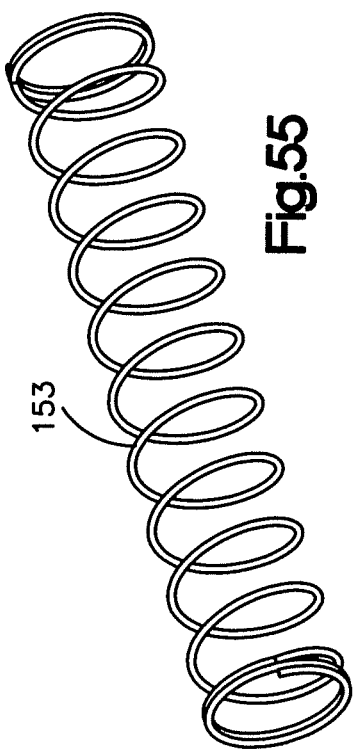

AUTOMATIC INJECTOR

CROSS-REFERENCE TO RELATED APPLICATIONS

This is a continuation of U.S. patent application Ser. No. 11/923,729, filed Oct. 25, 2007, now U.S. Pat. No. 7,794,432, which is a continuation of U.S. patent application Ser. No. 11/095,664, filed Apr. 1, 2005, now U.S. Pat. No. 7,449,012, which claims the benefit of U.S. Provisional Application No. 60/599,054, filed Aug. 6, 2004, wherein the entire contents of each are expressly incorporated herein by reference thereto.

FIELD OF THE INVENTION

The invention relates to an automatic injector or auto-injector for delivering medicament to an injection site. In particular, the invention is directed to an auto-injector having a needle cover mechanism to prevent a user from coming into contact with the needle of the auto-injector after use. The needle cover mechanism is held in a locked position prior to activation of the auto-injector. After injection, the needle cover mechanism is held in a locked deployed position such that the user cannot access the needle.

The invention is also directed to an auto-injector having a power pack containing a one-piece molded collet. The molded collet reduces the overall number of manufactured components while increasing versatility. The molded collet can be used with cartridges of varying sizes and different sized needles to vary the dosage amount of medicament delivered by the auto-injector.

BACKGROUND OF THE INVENTION

An automatic injector or auto-injector is a device designed to allow a user to self-administer a pre-measured dose of a medicament composition subcutaneously or intramuscularly, usually in an emergency situation. Automatic injectors are used, for example, to treat anaphylactic (severe allergic) reactions and to administer antidotes for certain poisons, such as chemical nerve agents and various drug compositions such as diazepam.

A typical auto-injector has a housing, inside of which is a cartridge. The cartridge has one or several chambers containing medicament compositions or components thereof and is adapted to be attached to a needle assembly. The cartridge can hold either a pre-mixed liquid medicament or a solid medicament and a liquid that are mixed prior to injection. The housing carries an actuation assembly with a stored energy source, for example, a compressed spring. Activation of the actuation assembly causes a sequence of movements, whereby the needle extends from the auto-injector into the user so that the medicament compound is then forced through the needle and into the user. After delivery of the dose of medicament into the injection site, the needle remains in an extended position. If the auto-injector is of the type designed to carry plural components of the medicament composition in separate, sealed compartments, structure may be included that forces the components to mix when the actuation assembly is activated.

There is a need for an auto-injector having a cover that provides adequate protection from the needle both prior to and after operation of the auto-injector. U.S. Pat. No. 5,295,965 to Wilmot et al. discloses an external cover member providing sharps protection for an auto-injector after use. The cover member is deployed after actuation of the auto-injector such that the user does not view the needle after use. The position of the cover member with respect to the auto-injector body is offset after use such that the needle cannot be redeployed through an opening in the needle cover.

U.S. Pat. No. 6,767,336 to Kaplan discloses a cover for an auto-injector. In an effort to reduce components, Kaplan eliminates an outer housing for the auto-injector. The cover is secured to the exterior of the cartridge holder sleeve. The cartridge holder sleeve includes several slots, which are sized to receive a latch on the cover. When the auto-injector is actuated, the cartridge within the cartridge holder sleeve causes the latch to be released from the recess such that the cover is free to travel under the bias of the spring. Since the cover disclosed by Kaplan is located on the exterior of the cartridge holder sleeve, it is possible for the user to grip the cover during operation of the auto-injector. As such, the user may prevent the latches from being released from the respective slots, which could prevent the cover from being properly deployed. This could impede the movement of the cartridge within the cartridge holder sleeve, which could result in the medicament being dispensed through the needle prior to the needle reaching the injection site. To overcome these deficiencies, higher trigger forces would be necessary. When the latches are released during the deployment of the cover, the latches are biased outwardly. It is possible for the user to be pinched or otherwise injured by this deployment.

If the cover deploys prior to delivery of the drug, a potentially life threatening event may arise because the user may not receive the proper dose of medicament. There is a need for a secured cover such that it cannot be displaced prior to use of the auto-injector. There is also a need for a cover that does not impede or adversely impact the operation of the auto-injector in the event it is contacted by the user. It is also desirable that the cover be locked in an extended position after use of the auto-injector so that the needle is not exposed such that a person cannot be accidentally pricked by the needle. It is also desirable to have a cover member having locking and deployment mechanisms that are protected against contact from the operator to prevent improper deployment of the cover.

SUMMARY OF THE INVENTION

One aspect of the present invention relates to an auto-injector for dispensing a predetermined dosage of a medicament. The medicament may be either self administered or administered by a caregiver. The auto-injector includes a housing. The housing is preferably oval or elliptical in shape such that it is more ergonomic. The oval shape prevents the auto-injector from rolling off a table or flat surface, while providing a larger surface area for printing user instructions. A cartridge container is disposed within the housing. A cartridge is received within the cartridge container. The cartridge has at least one opening therein and contains a medicament. The medicament is rearwardly confined by a plunger. The cartridge includes a needle assembly to dispense the medicament therethrough. The cartridge is advanced within the cartridge container from a stored position to an operation position where the needle extends from the cartridge container such that the dose of medicament can be administered. An actuation assembly or power pack provides a stored energy source that is capable of being released to drive the plunger within the cartridge to dispense the medicament through the needle assembly into the user and allowing the needle to be accessible on activation.

Another aspect of the auto-injector is the provision of a needle cover received within the housing. The needle cover shields the user from inadvertent exposure to the needle after use of the auto-injector providing sharps protection. Theoretically, the operation of the needle cover is fail safe because the cover will not deploy until after the needle penetrates the user. During operation, the needle of the cartridge extends through an opening in the needle cover to permit the dispensing of a dose of medicament. After use of the auto-injector, the needle cover is held in a locked position to prevent the cover from being retracted to expose the needle. According to another aspect of the invention, the needle cover has a locked retracted position prior to activation of the auto-injector, thus maintaining a compact configuration of the device prior to use. According to another aspect of the invention, the actuation forces associated with the auto-injector are not imparted on the needle cover.

In accordance with another aspect of the present invention, the auto-injector has a first locking assembly that holds the needle cover in the first locked position. The first locking assembly may be located on the cartridge container. The first locking assembly may include at least one locking tooth pivotally connected to the cartridge container or the needle cover. Each locking tooth releasably engages the needle cover and includes a locking surface constructed and arranged to contact a surface on the needle cover or the cartridge container. Each locking tooth may be formed as a separate component that is connected to the container or cover. It is contemplated that the locking teeth may be formed as integral parts of the needle cover or cartridge. A spring force of the locking tooth biases the locking surface into contact with the needle cover. The spring force may be provided by a spring portion of the locking tooth. The spring force may also be provided by a separate spring assembly biasing the locking surface into contact with the needle cover. Each locking tooth is preferably pivotally connected to the cartridge container. Each locking tooth pivots in response to movement of the cartridge within the cartridge container. It is also contemplated that the locking teeth can pivot in response to movement of the collet or the power pack. Typically, the locking surface pivots out of contact with the needle cover when the locking tooth pivots in response to the movement of the cartridge. The spring force and the force exerted by the locking teeth on the cartridge are controlled such that they negligibly or minimally impede the motion of the cartridge during the injection operation to avoid any premature rupturing of the diaphragm within the cartridge and premature administering of the medicament.

The needle cover is spring biased so that the cover is biased outwardly from the housing to cover the exposed needle after the first locking assembly is released. In accordance with another aspect of the present invention, the auto-injector has a second locking assembly that holds the needle cover in the second locked position. The second locking assembly may be located on the cartridge container, the outer body or the cover member. The second locking assembly may include at least one locking arm or wing preferably connected to the cartridge container. Each locking arm is spaced from the cartridge container such that the locking arm can be temporarily compressed against the cartridge container as the needle cover moves from the first locked position to the second locked position. Each locking arm has a locking surface to engage the needle cover when the needle cover is in the locked extended position. Each locking arm has a thick strut portion and a thin strut portion, wherein the thick strut portion is outwardly curved and the thin strut portion is inwardly curved. This construction maintains the locking arm in a normal uncompressed state to reduce stress on the cartridge container. This also permits a smooth deployment of the cover member. Furthermore, this arrangement ensures that the thick strut portion will buckle into a stable condition. This creates a stronger lock to prevent the cover member from being moved rearwardly to a retracted position. The inwardly curved nature of the thin strut portion allows the thick portion to buckle in a controlled manner to a stable condition. Additionally, the outwardly curved shape of the thick strut portion provides for fail safe locking of the cover member in the extended position. In the event that the thin strut breaks, the thick strut portion will still engage the cover member to maintain it in an extended locked position.

The cartridge container may further include at least one ledge extending outwardly therefrom. Each ledge is constructed and arranged to engage an edge of an opening in the needle cover to limit the travel of the needle cover with the respect to the cartridge container when the needle cover is in the extended position. When the ledge on the cartridge container engages the edge of the opening, the outward travel of the needle cover is limited. The second locking assembly limits the inward travel of the needle cover. The needle cover and the cartridge container contain openings formed therein. When the openings are aligned prior to activation of the auto-injector, user can view the contents of the cartridge through the housing and the openings. The housing may be transparent or opaque. When opaque, the housing may contain an opening that can be aligned with the openings in the needle cover and cartridge container so that the color of the medicament may be checked to determine whether or not the medicament is suitable for injection. If the medicament is discolored, the user will know not to administer the medicament. When the openings are not aligned after operation of the auto-injector, the user is no longer able to view the contents of the cartridge through the openings providing a visual indication to the user that the auto-injector has been used.

Another aspect of the present invention is the construction and arrangement of the actuation assembly or power pack, which is mounted within the housing adjacent to an open end. A release pin or safe pin is removably attached to the actuation assembly to prevent inadvertent actuation of the auto-injector when the release pin is in place. A pin or stem on the release pin is received within an opening in the actuation assembly to prevent actuation of the auto-injector. This opening in the power pack is spaced from the open end of the housing such that the opening is less visible to a user prior to administering the drug. This arrangement is provided so that user will not orient the incorrect end of the auto-injector against the injection surface of the user. The power pack is recessed or spaced from the end of the housing, which provides an indication to the user that pressing the power pack will not operate the auto-injector. The recessed nature of the power pack serves to hide the release pin hole in the power pack when the user is viewing the instructions on the outer body such that the user does not confuse the release pin hole with the opening through which the needle passes for administering the medicament. The release pin includes at least one tab extending therefrom. The tab is compression fit into a complimentary recess formed in the actuation assembly to prevent the inadvertent removal of the release pin. The tabs also prevent rotation of the release pin such that the user easily recognizes that the release pin must be pulled in order to be removed.

The actuation assembly includes an outer body, which is configured to engage the release pin. The outer body is constructed to be connected to the housing. An inner body is operatively coupled to the outer body. At least one retention tab on the inner body secures the inner body to the outer body. The inner body is capable of limited movement with respect to the outer body. A collet is operatively coupled to the inner body. An energy source is operatively connected to the inner body and the collet. Unlike conventional collets, the collet in the present invention is molded as a single piece. No spacers or other components are provided between the collet and the plunger in the cartridge. This arrangement simplifies construction. Different sized collets can be produced and installed into the actuation assembly, such that only the collet needs to altered when different sized cartridges are used or a different sized dosage of medicament is to be administered.

BRIEF DESCRIPTION OF THE DRAWINGS

An understanding of the various embodiments of the invention may be gained by virtue of the following figures, of which like elements in various figures will have common reference numbers, and wherein:

FIG. 2 is a side cross sectional view of the auto-injector of FIG. 1 in an unactivated state having the release pin in place;

FIG. 3 is a side schematic view of the auto-injector in the unactivated state of FIG. 2;

FIG. 5 is a side cross sectional view of the auto-injector of FIG. 1 wherein the needle cover spring is in a compressed state;

FIG. 6 is a side schematic view of the auto-injector of FIG. 5;

FIG. 7 is a side cross sectional view of the auto-injector in an actuated state with the needle in a drug delivery position;

FIG. 8 is a side schematic view of the auto-injector of FIG. 7;

FIG. 12 is a left front schematic view of the auto-injector of FIG. 1 having the outer body removed wherein the needle cover is located in a retracted position prior to activation of the auto-injector, FIG. 13 is an enlarged view of FIG. 12 illustrating the position of the locking wings of the cartridge container and the locking teeth;

FIG. 14 is a left front schematic view of the auto-injector of FIG. 1 having the outer body removed when the needle cover is located in an extended protective position after use of the auto-injector, FIG. 15 is an enlarged view of FIG. 14 illustrating the position of the locking wings of the cartridge container and the locking teeth;

FIG. 17 is a left rear perspective view of the power pack outer body for the power pack for the auto-injector according to the present invention;

FIG. 18 is a side perspective view of the collet for the power pack for the auto-injector according to the present invention;

FIG. 19 is a right front perspective view of the power pack inner body for the power pack for the auto-injector according to the present invention;

FIG. 20 is a side perspective view of the spring assembly for the power pack for the auto-injector according to the present invention;

FIG. 21 is a left bottom perspective view of the release pin for the auto-injector according to the present invention;

FIG. 29 is a partial cross sectional perspective view illustrating the interior of the power pack inner body;

FIG. 30 is side perspective view of the power pack inner body;

FIG. 31 is a bottom perspective view of the power pack inner body;

FIG. 32 is a side view of the release pin;

FIG. 33 is another side view of the release pin of FIG. 32 rotated 90° about an axis;

FIG. 34 is a bottom perspective view of the safe pin of FIG. 32;

FIG. 35 is a side view of the collet of the power pack;

FIG. 36 is another side view of the collet of FIG. 35 rotated 90° about an axis;

FIG. 37 is an enlarged end view of the collet illustrating the stabilizing arch;

FIG. 39 is a cross sectional view of the cartridge container and needle cover located within the outer body with the power pack removed prior to final assembly of the auto-injector;

FIG. 40 is a cross sectional view of the cartridge container and needle cover located within the outer body of FIG. 39 rotated 90° about an axis with the power pack removed prior to final assembly of the auto-injector;

FIG. 42 is a perspective view of the needle cover spring;

FIG. 43 is a front left side perspective view of the needle cover of the auto-injector;

FIG. 44 is a front left side perspective view of the outer body of the auto-injector;

FIG. 45 is another left side perspective view of the outer body of FIG. 44;

FIG. 46 is a partial cross sectional perspective view illustrating the interior of the outer body;

FIG. 47 is a side view of the outer body;

FIG. 48 is another side view of the outer body of FIG. 47 rotated 90° about an axis;

FIG. 52 is an enlarged side view of the cartridge container illustrated in FIG. 51, wherein the dotted lines illustrate the deflection path of the locking wings;

FIG. 53 is a right rear perspective view of the needle cover of the auto-injector, FIG. 54 is a side view of the needle cover of FIG. 53;

FIG. 55 is a perspective view of the needle cover spring;

DETAILED DESCRIPTION OF A PREFERRED EMBODIMENT OF THE INVENTION

It should be appreciated that some of the components described herein are conventionally known in the broader aspects, as described in U.S. Pat. No. 4,031,893 ("the '893 patent") hereby incorporated by reference in its entirety, and thus not described in unnecessary detail here. It should also be appreciated that known modifications or variations to the '893 patent can apply equally to the auto-injector of the present invention as will be described below. These modifications or variations include embodiments described in U.S. Pat. Nos. 4,226,235; 4,329,988; 4,394,863; 4,723,937; and U.S. Ser. Nos. 09/985,466; 10/285,692, each of which is incorporated by reference in its entirety for the full teachings therein.

Figure 1:
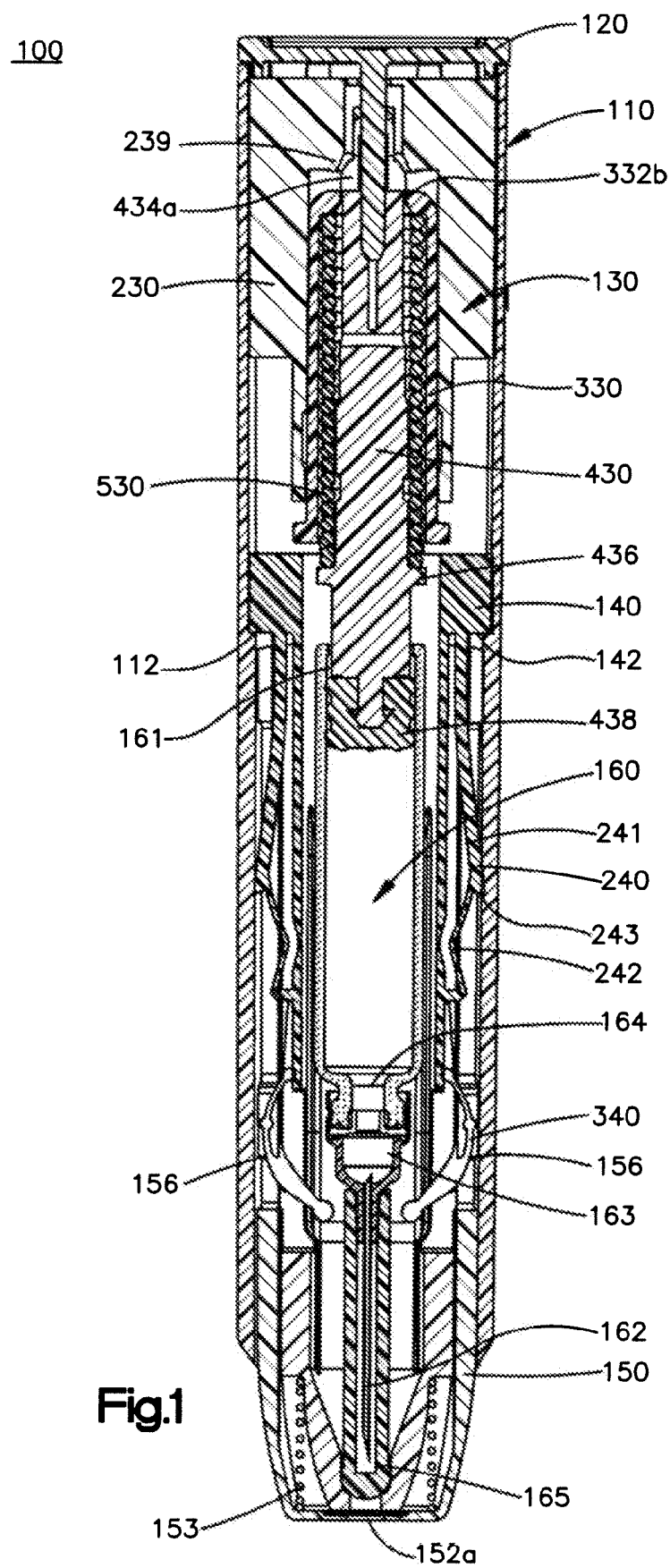
FIG. 1 is a side cross sectional view of the auto-injector according to an embodiment of the present invention.
Figure 59:
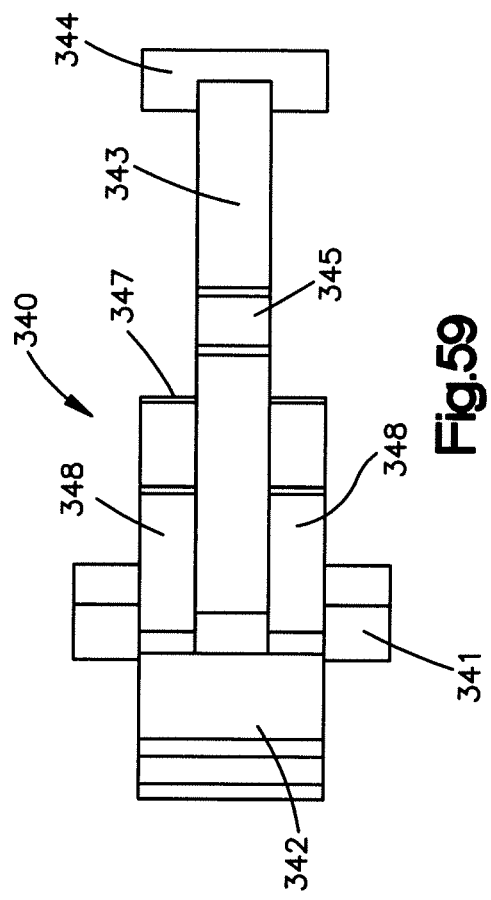
FIG. 59 is a top view of the locking tooth.
Figure 56:
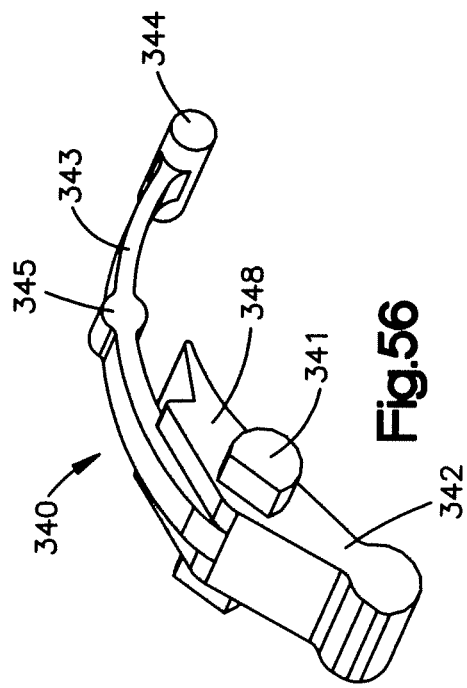
FIG. 56 is a right top perspective view of a locking tooth of the auto-injector in accordance with the present invention.
Figure 57:
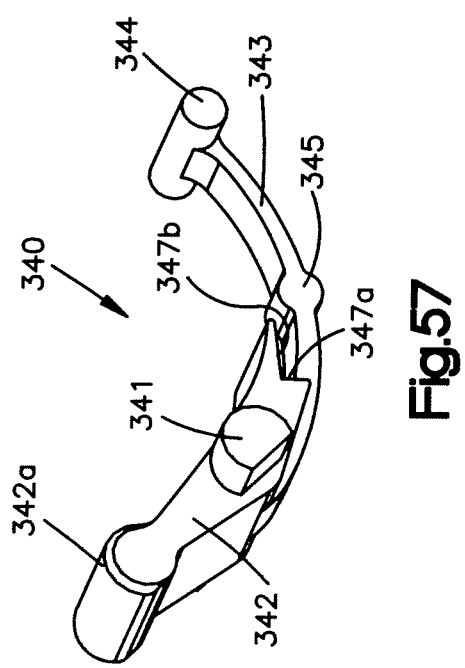
FIG. 57 is a left bottom perspective view of the locking tooth of FIG. 55.

An auto-injector 100 of the present invention will now be described in greater detail in connection with FIGS. 1-59. The auto-injector 100 includes an outer body 110, a release pin 120, a power pack 130, a cartridge container 140, a needle cover 150 and a cartridge 160 housing a dose of medicament. The dose can be stored in liquid or solid form or as a combination of a liquid and a solid that is mixed prior to injection.

The auto-injector 100 includes an outer body 110 shown in FIGS. 38 and 44-48. The outer body 110 has a generally oval or elliptical shape, which is more ergonomic sized to permit easy grasping and use by the user or caregiver in comparison with a cylindrical body. The generally oval shape of the outer body 110 prevents the auto-injector 100 from inadvertently rolling or sliding off a flat surface. Furthermore, the oval shape provides a larger print surface for labeling the auto-injector 100 with instructions. The outer body 110 is preferably formed from a synthetic material such that it can be easily molded. The outer body 110 can be transparent such that the interior components can be easily viewed through the outer body 110. With such a construction, the user can view the contents of the cartridge 160 through windows 141a and 141b in the cartridge container 140 and the needle cover 150 at predetermined times. It is also contemplated that the outer body 110 can be opaque such that the interior components are not visible through the outer body 110. It is also contemplated that the outer body 110 has a window or windows that permit viewing of the components within the outer body 110. The outer body 110 has an opening 111 formed in one end that is sized to receive a release pin 120. When in place, the release pin 120 prevents inadvertent use or activation of the auto-injector 100. The release pin 120 is illustrated in FIGS. 32-34. It is contemplated that operating instructions may be printed directly onto the outer body 110. It is also contemplated that a label may be affixed to the outer body 110, which may increase the rigidity of the outer body 110. When the outer body 110 includes one or more apertures, the provision of a label increases the strength of the outer body 110, which makes the provision of additional structural reinforcements unnecessary.

The opening 111 includes side recesses 111a and 111b, which extend downwardly along opposing sides of the outer body 110, shown in FIGS. 45, 46 and 48. While two recesses are shown, it is contemplated that a single recess may be provided or more than two may be provided. The number of recesses will correspond to the number of tabs. The recesses 111a and 111b are sized so that they may receive downwardly extending tabs 121a and 121b on the release pin 120. The tabs 121a and 121b prevent rotation of the release pin 120 such that the user easily recognizes that the release pin 120 is to be pulled rather than rotated to permit removal of the release pin 120 in order to actuate the auto-injector 100. The tabs 121a and 121b are primarily received in retention recesses 235 located on opposing sides of the power pack 130, described in greater detail below. The recesses 111a and 111b provide access to the tabs 121 in the recesses 235. The tabs 121a and 121b are compression fit onto the power pack 130 to prevent inadvertent removal. To release the pin 120, the operator compresses or pinches the tabs 121 to dislodge the edges of the tabs 121 from the recesses 235 such that the pin 120 can then be pulled/removed from the power pack 130. As shown, the tabs 121 have a curvature which creates a chamfered edge that engages the edges of the recesses 235. The shape of the tabs 121 and the recesses 235 are full complimentary, which creates the friction or compressive retaining force between the pin 120 and power pack 130. The release pin 120 also includes downwardly projecting ribs 122a and 122b, which are adapted to be received on the top surface of the power pack 130. The ribs 122a and 122b increase the stability and rigidity of the release pin 120. It is contemplated that additional ribs may be provided. The release pin 120 includes an outwardly facing flat end 123 having a peripheral ledge 124. The peripheral ledge 124 permits grasping of the release pin 120 by the user. The ledge 124 is sized to rest on the end surface of the outer body 110 adjacent opening 111. The release pin 120 includes a downwardly extending pin 125, which engages the collet 430 of the power pack 130. When secured in place (i.e., prior to removal of the release pin 120 and prior to actuation of the auto-injector 100), the pin 125 prevents the end of the collet 430 from compressing, which prevents actuation of the auto-injector 100. The end 123 has a shape corresponding to the oval/elliptical shape of the outer body 110.

As shown in FIG. 46, the inner surface of the outer body 110 is contoured to receive the power pack 130, a cartridge container 140 and a needle cover therein 150. Unlike many prior art needle covers, the needle cover 150 is positioned between the container 140 and the outer body 110 such that the user does not contact the cover 150 during the operation, which could impede the deployment of the cover or cause a diaphragm within the cartridge to rupture prematurely. Additionally, the mechanisms for locking and deploying the cover member are located within the outer body 110 and are thus protected against tampering and dirt ingress. The outer body 110 includes a cartridge container retention step 112 formed on the inner surface near the end of the outer body 110 adjacent the opening 111. A ledge 142 of the cartridge container 140 abuts the retention step 112 to limit the downward movement of the cartridge container 140 within the outer body 110 once the auto-injector 100 has been assembled such that the container can not be moved out of opening 114. A plurality of power pack retention openings 113a, 113b and 113c are formed on at least one side of the outer body 110. Projections or teeth 238 on the power pack 130 are snap fit into the openings 113. This snap fit prevents the removal of the power pack 130 from the outer body 110 once installed in the outer body 110. The power pack outer body 230 is not movable with respect to the outer body 110. The ledge 142 of the cartridge container 140 is sandwiched between the retention step 112 and the power pack 130.

An opening 114 is formed in the outer body 110 on an end opposite the opening 111. The opening 114 is configured such that a portion of the cartridge container 140, a portion of the needle cover 150 can extend therefrom. The step 112 limits the travel of the container 140 through opening 114. The end of the outer body 110 is intended to be orientated adjacent the injection surface of the user such that end portion of the cover 100 contacts the injection surface.

The power pack 130 will now be described in greater detail in connection with FIGS. 17-20, 22-31 and 35-37. The power pack 130 includes a power pack outer body 230, a power pack inner body 330, a collet 430, and a power pack spring assembly 530. The activation force necessary to release the energy stored in the power pack is between 4 to 8 pounds. The activation force is the force required to release the collet 430 from the inner body 330 when the auto-injector 100 is pressed against the injection surface. The injection force provided by the spring assembly 530 is approximately 30 pounds. The injection force must be sufficient such that the cartridge 160 is advanced within the cartridge container 140 to drive the needle such that it pierces the sheath to permit injection of the medicament into the user. The power pack outer body 230 is a generally cylindrical elongated hollow body 231. A plurality of outer peripheral ribs 232a, 232b and 232c extend outwardly from an outer surface of the hollow body 231. While these ribs 232 are shown, it is contemplated additional ribs may be provided. The ribs 232 are provided to prevent distortion of the outer body 110 of the auto-injector 100. A plurality of outer longitudinal ribs 233a, 233b are spaced about the outer surface of the hollow body 231. The ribs 233 cooperate with the ribs 232 to further strengthen the auto-injector 100 and prevent distortion of the outer body 110 when gripped and used by a user.

One of the peripheral ribs 232a forms a top end surface 237 of the power pack outer body 230. A hole 234 is provided in end surface which is sized to receive the downwardly extending pin 125 of the release pin 120. Retention recesses 235a and 235b are formed on opposing sides of the hollow body 231 adjacent the top end surface. The recesses 235a and 235b are formed by walls 236a and 236b which extend outwardly from the hollow body 231 and upwardly from the top end surface 237 of the peripheral rib 232a. The recesses 235a and 235b are aligned with the side recesses 111a and 111b of the outer body 110 such that when the release pin 120 is secured to the auto-injector 100, the tabs 121a and 121b are received in both recesses 235a and 235b. The recesses 235a and 235b are sized to apply a compressive force on the tabs 121a and 121b to secure the release pin 120 in place to prevent inadvertent removal.

Figure 26:
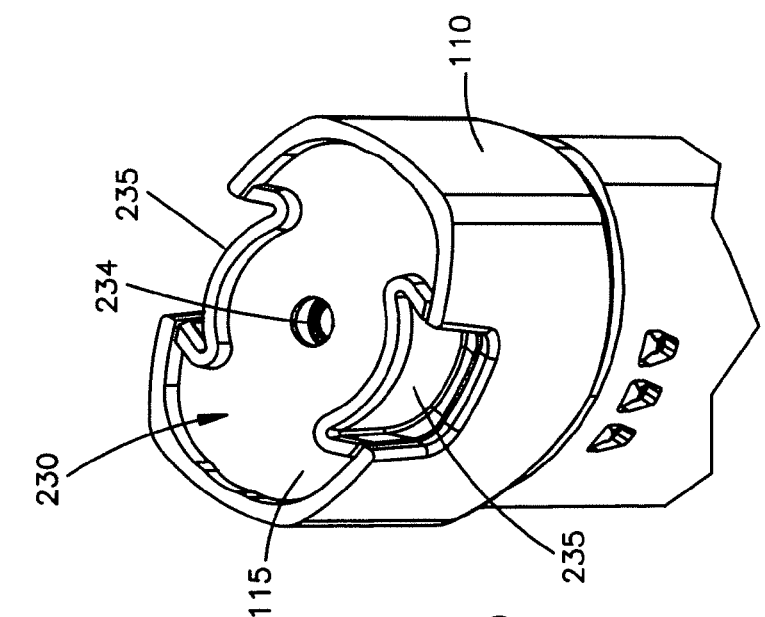
FIG. 26 is a top left perspective view of the power pack positioned within the outer body having the safe pin removed.
Figure 25:
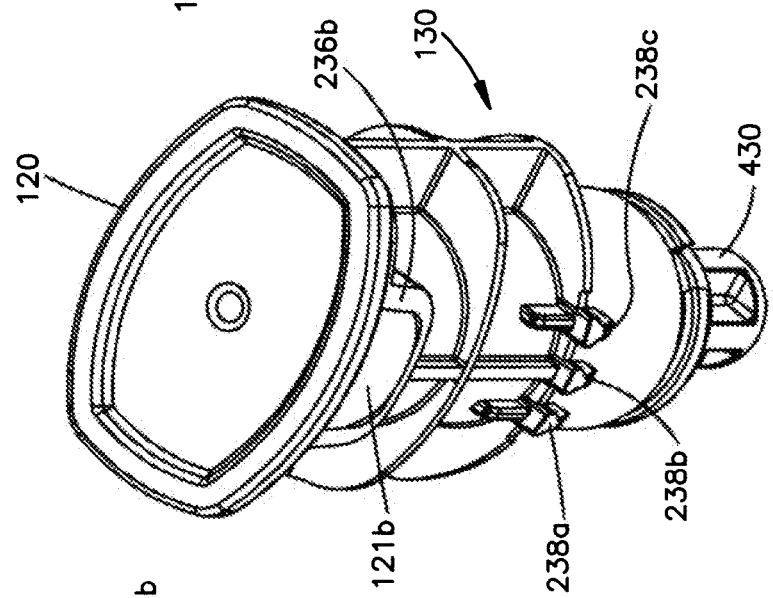
FIG. 25 is a top left perspective view of the power pack of FIG. 22.
Figure 24:
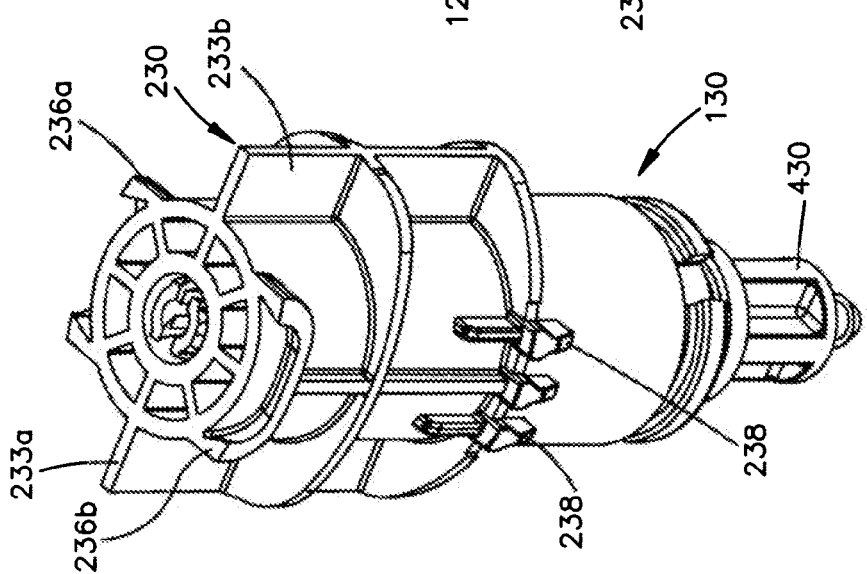
FIG. 24 is a top left perspective view of the power pack of FIG. 22 having the top portion of the release pin and a peripheral rib of the power pack outer body removed.
Figure 27:
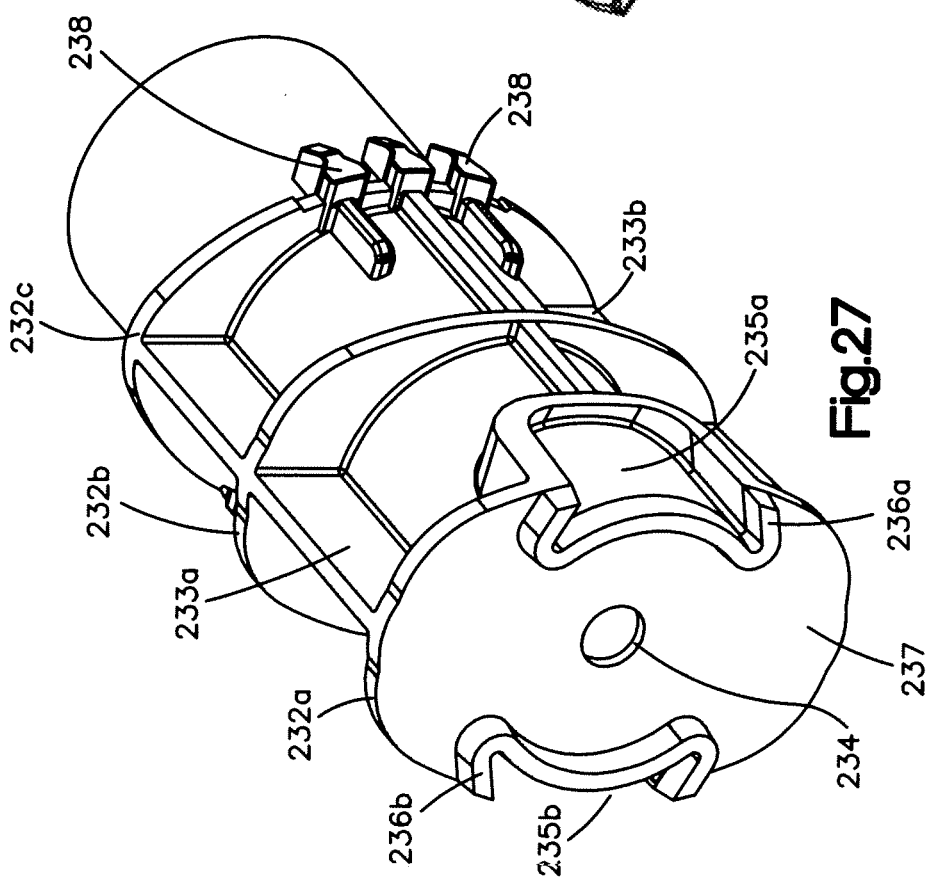
FIG. 27 is left side perspective view of the power pack outer body
Figure 38:
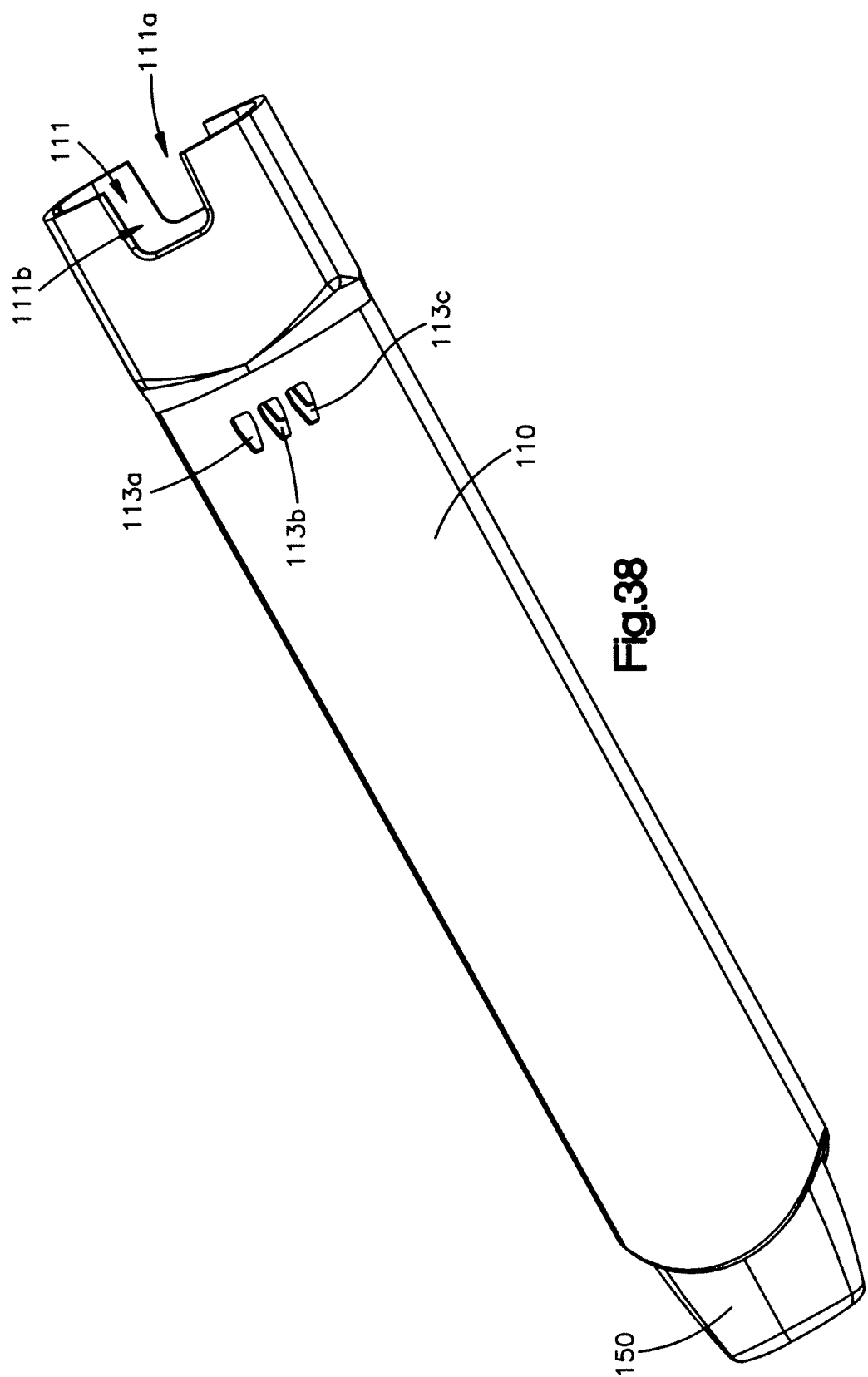
FIG. 38 is side perspective view of the needle cover located within the outer body of the auto-injector.
Figure 41:
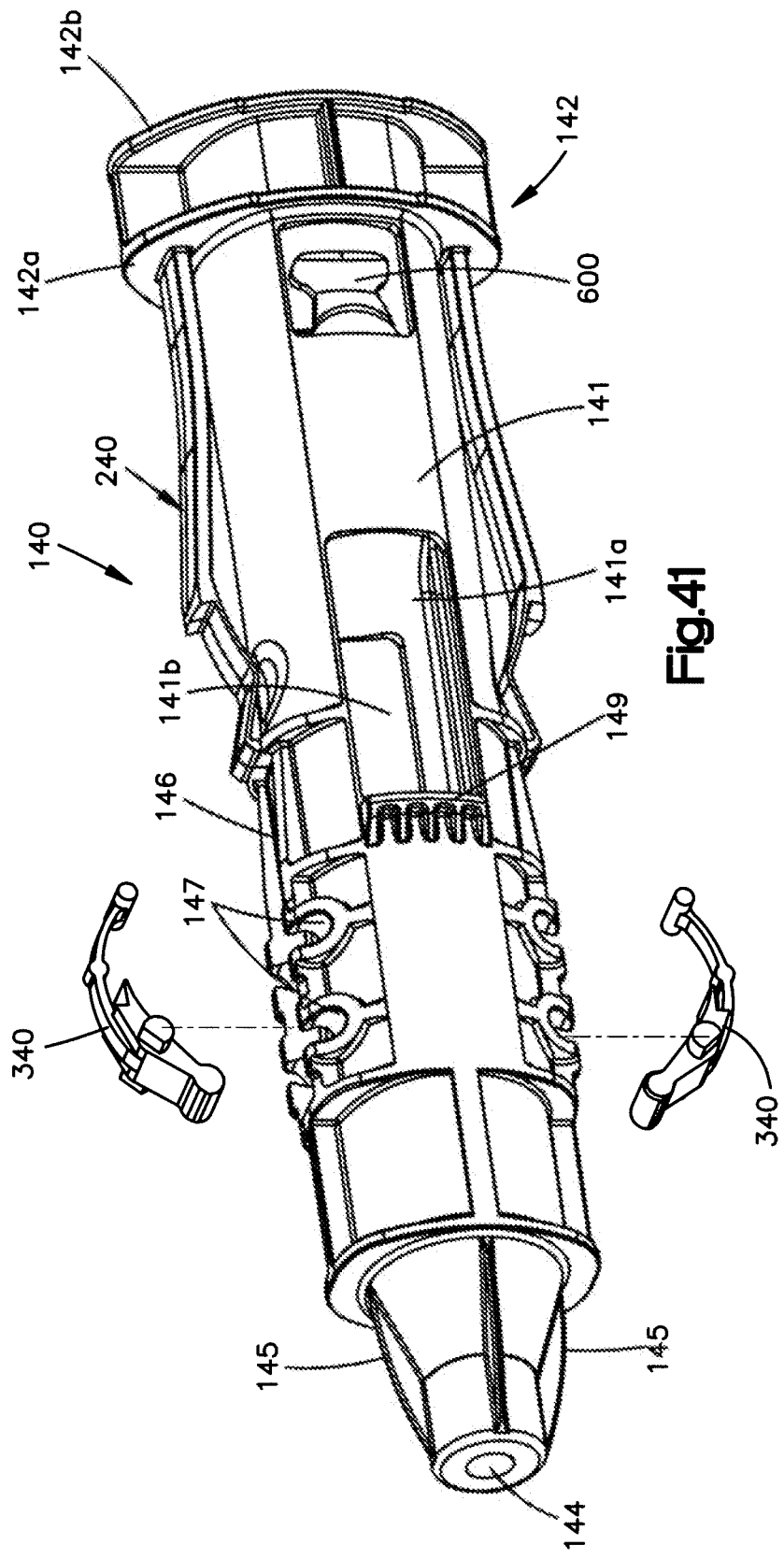
FIG. 41 is a front left side perspective view of the cartridge container of the auto-injector.

As shown in FIGS. 17, 26 and 27, the walls 236a and 236b extend upwardly from the end surface 237 of the peripheral rib 232a. With such an arrangement, the end surface 237 is spaced or recessed below the end surface of the outer body 110, as shown in FIG. 26, forming a recess 115. The recess 115 reduces and/or avoids the visual effect of a push button. As such, the user will not be inclined to press the end surface 237 to administer the medicament. Additionally, it provides a visual indication to the user that the recess 115 is located at the inoperative end of the auto-injector 100 such that the user is inclined to place the cover 150 against the injector surface not the opposite end of the auto-injector. The recess 115 also serves to space the hole 234 from the end of the auto-injector 100 to deemphasize the presence of the hole 234 such that it is hidden when the user reads the label on the outer body 110. As such, the user is disinclined to position the hole 234 adjacent the injection site. This arrangement is just one countermeasure provided to insure against improper use of the auto-injector 100. The ribs 122a and 122b of the release pin 120 are received within the recess 115.

A plurality of projections or teeth 238a, 238b, 238c are formed on the outer surface of the hollow body 231. The teeth 238a, 238b, 238c are sized to be snap fit into the openings 113a, 113b, 113c to secure the power pack 130 within the outer body 110. This construction permits these components 110 and 130 to be secured together without the need of an adhesive of other form of bonding. A corresponding set of teeth 238 may be provided on the opposite side of the hollow body 230 to match the corresponding openings in the outer body 110.

Figure 28:
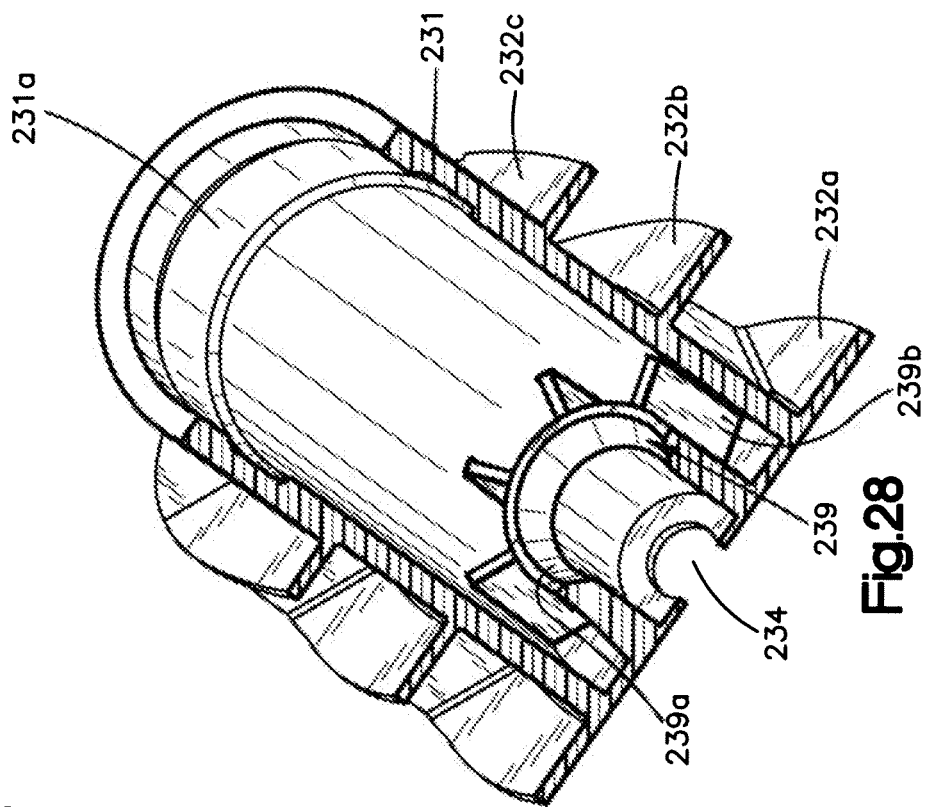
FIG. 28 is a partial cross sectional perspective view illustrating the interior of the power pack outer body.

The interior of the hollow body 231 includes a recess 231a, which is sized to receive a retention tab 334 on the power pack inner body 330. The recess 231a may be a groove, which extends about the inner periphery of the hollow body 231. The recess 231a is positioned in the hollow body 231 near an end opposite the end surface 237. As seen in FIGS. 1 and 28, a collet activation structure 239 extends into the interior of the hollow body 231 from the inner side of the end surface 237. The collet activation structure 239 has a generally cylindrical shape with a sloped collet activation surface 239a located on a free end. The activation surface 239a is provided such that when the pin 120 is removed and the front end of the injector is forced into an injection site so that cartridge container 140 rearwardly moves to engage inner body 330, this will rearwardly force the arrowheads 434 and particularly rearward surface 489 thereof (see FIG. 35) into engagement with surface 239a to force the arrowheads 434 of the collet 430 together to release the spring assembly 530 and thus release the necessary energy to inject the medicament into the user. Ribs 239b may be provided to reinforce the collet activation structure 239. It is contemplated that other means of releasing the collet 430 may be employed. A push button type actuation arrangement may be employed, which is described in greater detail in U.S. Pat. No. 4,031,893 and hereby incorporated in its entirety by reference.

The power pack inner body 330 is a generally cylindrical hollow inner body 331. The hollow inner body 331 has an opening 332 formed in one end. The opening 332 has a collet assembly lead-in surface 332a which is used to compress a portion of the collet assembly 430 during assembly of the auto-injector 100 such that is can be properly mounted within the power pack inner body 330. The opening 332 also has a collet retention surface 332b located on an opposite edge which support the opposing arrowheads 434 of the collet 430 prior to activation. The hollow inner body 331 has an opening 333 formed on an opposing end. Spaced from the opening 333 are a plurality of retention tabs 334 which are sized to be snapped into the retention recess 231a. The recess 231 and tabs 334 permit limited movement between the power pack inner body 330 and the power pack outer body 230. The arrangement is also beneficial for purposes of assembling the auto-injector 100. The inner body 330 and the outer body 230 can be preassembled. The recess 231 and tabs 334 maintain the inner body 330 and the outer body 230 in proper alignment for assembly. Furthermore, this arrangement prevents the subassembly of the inner body 330 and the outer body 230 from separating prior to the final assembly in the auto-injector 100. It is also contemplated that other means which permit limited movement between the outer power pack and the inner power pack, which secure the components together may be employed. A ledge 335 at least partially extends about the periphery of the opening 333. The ledge 335 is sized to engage the cartridge container 140 and the power pack outer body 230 at certain times during the operation of the auto-injector 100, described in greater detail below. A spacing exists between the inner power pack 330 and the cartridge container 140 after assembly and prior to activation of the auto-injector 100 to create a gap, which avoids permanently putting forces on the power pack and the spring 530.

A collet 430 is received within the hollow interior of the power pack inner body 330. The collet 430 preferably is a molded one piece construction. The collect 430 has an elongated body 431 having an opening 432 formed therein which forms a pair of side arms 433a and 433b. Each side arm 433a and 433b includes an arrowhead detail 434a and 434b respectively. One side of each arrowhead 434a and 434b is configured to contact and engage the collet retention surface 332b. An opposite side of each arrowhead 434a and 434b is configured to engage the collet assembly lead-in surface 332a, which permits the side arms 433a and 433b to be deflected inwardly to permit operation of the auto-injector 100. The end 435 of the collet 430 adjacent the arrowheads 434a and 434b includes an opening 435a sized to receive the pin 125 of the release pin 120. The pin 125 prevents the side arms 433 from being deflected inwardly towards each other. When secured in place, the pin 125 prevents activation of the auto-injector 100. The opening 432 has an arch 432a formed on one end, as shown in FIG. 37. The arch 432a helps stabilize the side arms 433 and assist them in springing apart when the arms have been compressed together. The arch 432a reduces the amount of stress on the collet.

The collet 430 is positioned within the power pack spring assembly 530. One end of the spring assembly 530 is supported on a flange 436 formed on the collet 430. The flange 436 extends outwardly from the elongated body 431. While the flange 436 supports one end of the spring assembly 530, the location of the flange 436 on the body 431 can also serve to define the delivered dose volume of medicament injected into the user. In certain applications it is desirable to control the amount of medicament delivered through the needle such that a portion of the medicament remains in cartridge 160. The flange 436 may limit the distance that the collet 430 can travel into the cartridge 160, which contains the liquid medicament. As such, the amount of medicament delivered is controlled. In this arrangement, the flange 436 is sized to contact the end of the cartridge 160. For larger diameter cartridges and for larger doses of medicament, it is contemplated that the flange 436 can travel within the cartridge 160. The collet 430 further includes a projection 437, which receives a plunger 438. The plunger 438 is slidably received within the cartridge 160. In other applications, it is desirable to dispense all of the medicament from the container 160. A small residual amount of medicament remains in the needle 162 and the neck of the cartridge 160 adjacent the needle 162. In these applications, the flange 436 travels within the interior of the cartridge 160 so that the plunger 438 travels the length of the interior of the cartridge 160 to dispense all of the medicament (except for the residual amounts mentioned above) through the needle 162. It is contemplated that different sized collets 430 may be used in the present auto-injector 100. As such, the collet 430 can be changed based upon cartridge size and desired dose.

The collet 430 is preferably formed as a single piece from a suitable plastic material. The one piece collet 430 simplifies manufacturing and lowers costs by reducing the number of components needed to form a collet. In conventional collets, multiple brass components may be used. In addition in other auto-injectors, a spacer has been required for use in conjunction with the collet 430 to accommodate different amounts of medicament for different auto-injectors. The collet 430 in accordance with the present invention eliminates the multi component construction and also advantageously eliminates the need for a spacer. The length of the collet can be selected based upon the desired dosage. This construction further permits the elimination of a metal insert typically found in the plunger and a firing seat above the power pack inner body. It is contemplated that the size and shape of the collet 430 itself may be varied to accommodate different sized cartridges 160. When the flange 436 does not contact the cartridge 160, it is possible to dispense the entire contents of the cartridge 160 except for any residual amounts remaining in the needle or in the neck of the cartridge 160. It is contemplated that a nipple plunger, as disclosed in U.S. Pat. No. 5,713,866 to Wilmot, the disclosure of which is hereby incorporated specifically herein by reference, may be employed to prevent any buildup of residual amounts of medicament in the neck of the cartridge 160. The position of the flange 436 can be varied to control the amount of dosage injected into the user when the flange is positioned such that the collet and the plunger 438 travel a greater distance within the cartridge 160 before the flange 436 contacts the cartridge 160, a larger dose is dispensed. The length of the collet 430 and the diameter of the cartridge 160 can be selected to control the flow of fluid through the needle 162 of the cartridge 160 so that a desired flow rate is obtained. The auto-injector 100 in accordance with the present invention is configured such that collets 430 of varying sizes can be used within the same outer body 110 and the power pack 430.

An opposite end of the spring assembly 530 rests against an inner surface of the power pack inner body 330 against opening 332.

The cartridge container 140 will now be described in greater detail in connection with FIGS. 41 and 49-52. The cartridge container 140 has a generally elongated hollow body 141 sized to be received within the outer body 110. A ledge 142 is formed on one end of the elongated body 141. The ledge 142 contacts the retention step 112 formed on the inner surface of the outer body 110. The ledge 142 limits the downward movement of the cartridge container 140 within the outer body 110 such that it cannot be removed through opening 114. The ledge 142 is formed by peripheral ribs 142a and 142b, which extend outwardly similar to the ribs 232a, 232b and 232c on the power pack outer body 230. The ribs 142a and 142b also prevent distortion of the outer body 110.

The elongated hollow body 141 has a hollow interior sized to receive the cartridge 160 therein. The hollow body has an opening 143 such that the cartridge 160 can be located in the hollow interior and to permit the collet 430 to be slidably received within the cartridge 160. The cartridge container 140 and the locking teeth 340 thereof are designed to accommodate various sized cartridges 160, while maintaining full needle cover functionality. As such, a common design needle cover assembly (including the cartridge container and locking teeth) can be used for various different volumes of drugs and different sized needles. For longer and larger cartridges, it is desirable to provide additional support to prevent axial and radial movement, which could damage or fracture the cartridge 160. A pair of tabs 600 are formed on the hollow body 141 to apply a compressive force on the cartridge 160 to hold and align the cartridge 160 in a proper orientation to prevent such axial and radial movement. The tabs 600 provide friction to prevent movement of the cartridge 160 within the hollow body 141 during shock loading to prevent the cartridge from being dislodged or moved forward with the cartridge holder 140 prior to the medicament dispensing sequence. Typically, the smaller cartridges do not contact the tabs 600. The collet 430 and the needle and needle sheath provide sufficient support for the cartridge. The end of hollow body 141 has a tapered construction with an opening 144 sized to permit the passage therethrough of the needle 162 and protective sheath 165 of the cartridge 160. A plurality of ribs 145 are formed on the outer surface of the hollow body 141 on the tapered end. The ribs 145 help stabilize the needle cover spring 153 of the needle cover 150. The ribs 145 also serve as guides to aid in the assembly of the auto-injector 100.

The elongated hollow body 141 has at least one viewing window 141a and 141b formed therein. The viewing windows 141a and 141b permit the user to view the contents of the cartridge 160 before activation of the auto-injector 100 to insure that the medicament has not become contaminated or expired.

A pair of locking arms or wings 240 extend from the ledge 142 and are connected to a mid-portion of the hollow body 141, as shown in FIG. 52. Each locking wing 240 has a thickened strut 241 having a generally curved shape, as shown in FIG. 52. The thickened strut 241 is curved such that when a compressive load is applied to the locking wing 240 (e.g., when a user is attempted to push the needle cover 150 back into the outer body 110 after use of the auto-injector 100) the thickened strut 241 bends in the manner illustrated by the dashed lines in FIG. 52. With such a construction, the locking wings 240 are supported by the body 141 of the cartridge container 140, which increases the compressive strength of the locking wings 240. While not preferred, it is contemplated that a single locking wing 240 can be provided.

Figure 9:
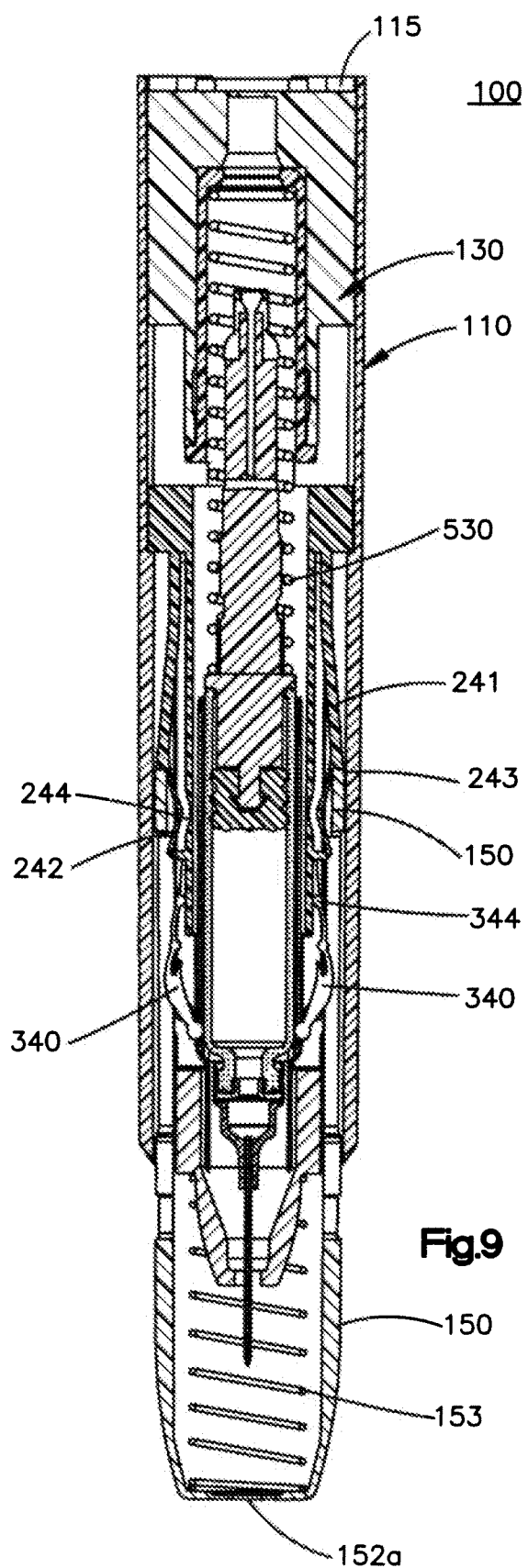
FIG. 9 is a side cross sectional view of the auto-injector following delivery of the drug wherein the needle cover is in an extended protective state.
Figure 10:
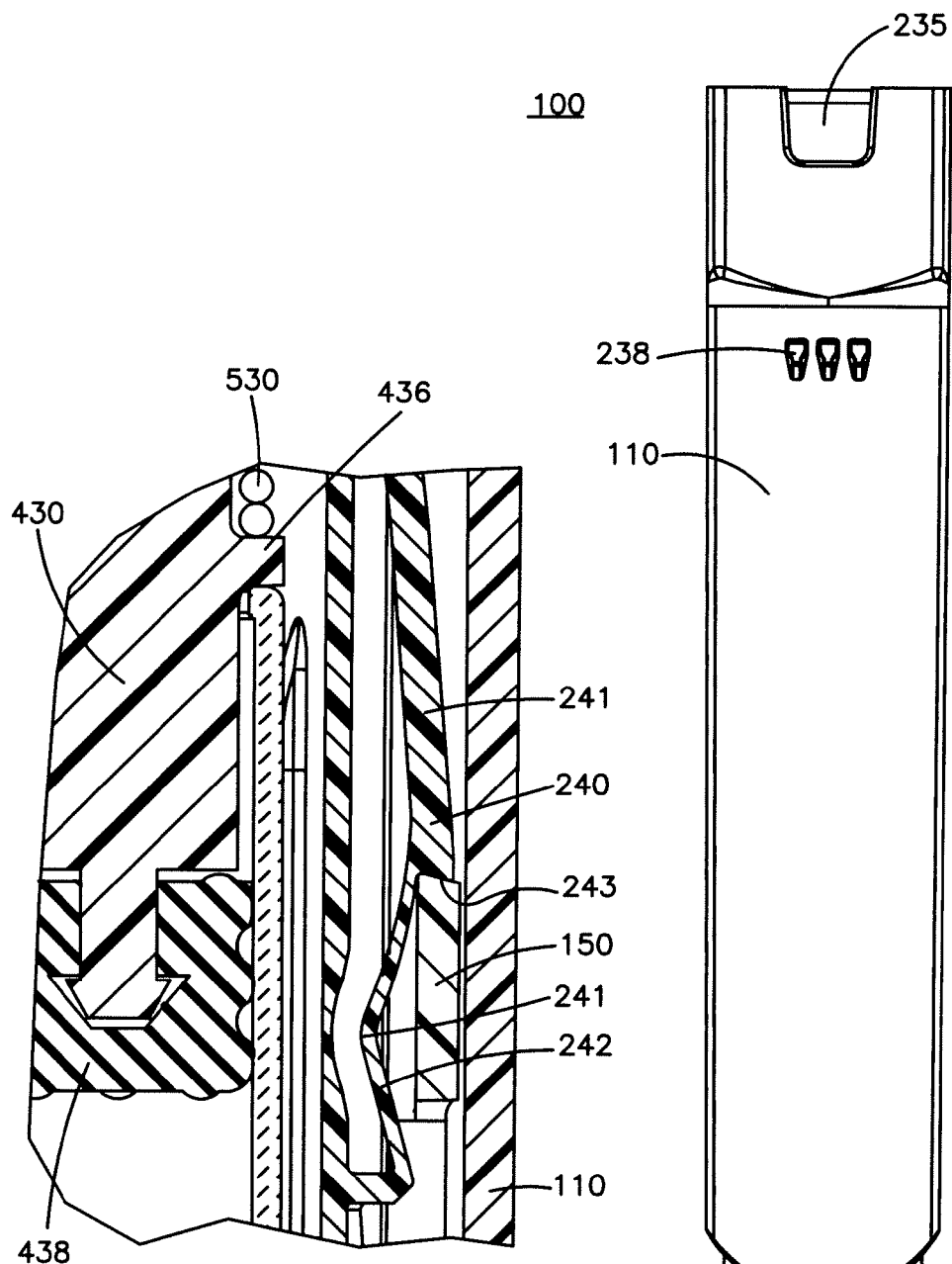
FIG. 10 is an enlarged view of the locking wings of the cartridge container when the needle cover is in the extended protective state, as shown in FIGS. 9 and 11.

A thinner strut 242 extends from the free end of the strut 241 and is connected to the body 141 of the cartridge container 140. A locking surface 243 is formed at the intersection of struts 241 and 242. The locking surface 243 engages a surface on the cover 150 to limit the inward travel of the cover 150 after operation of the auto-injector 100, as shown in FIGS. 9 and 10. The thinner strut 242 provides a spring force to keep the thicker strut 241 biased in an outwardly direction. The thinner strut 242 also provides tensile strength under extreme loads and helps prevent the strut 241 from collapsing in a sideways direction because the thinner strut 242 remained retained in a guide groove in the needle cover 150 after the cover member 150 has moved to an extended position. The curved shape of the strut 242 permits the strut 242 to bend inwardly as shown in the dashed lines in FIG. 52. This prevents the entire wing 240 from forming a rigid arch. Thus allowing the thicker strut 241 to flex inwardly towards the body 141 without causing excessive compressive leads along the wing 240. It is contemplated that the locking arm 240 may be located on the outer body 110.

As shown in FIGS. 39, 41, 49, 50 and 52, the elongated body 141 of the cartridge container 140 includes a recess 244 located between the thinner strut 242. If the locking arms 240 are located on the outer body 110, the recess 244 could be formed in the outer body 110. Alternatively, an opening in the outer body 110 could also be provided. This recess 244 increases the distance that the thinner strut 242 travels inwardly toward the body 141, which increases the spring force provided to the thicker strut 241 to maintain the strut 241 in an outwardly biased position. The locking wings 240 are normally maintained in unstressed states. The locking wings 240 are compressed temporarily as the needle cover 150 passes over them. The locking wings 240 spring out such that the locking surface 243 engages the cover member 150 to prevent the needle cover 150 from being pushed backwards as shown in FIG. 10.

Figure 49:
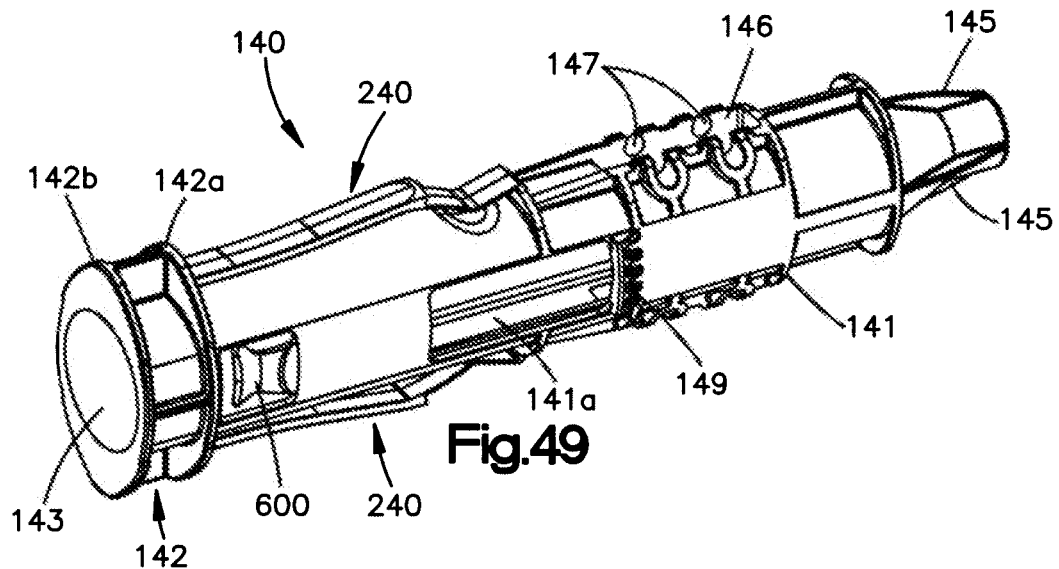
FIG. 49 is a right rear side perspective view of the cartridge container of the auto-injector.
Figure 50:
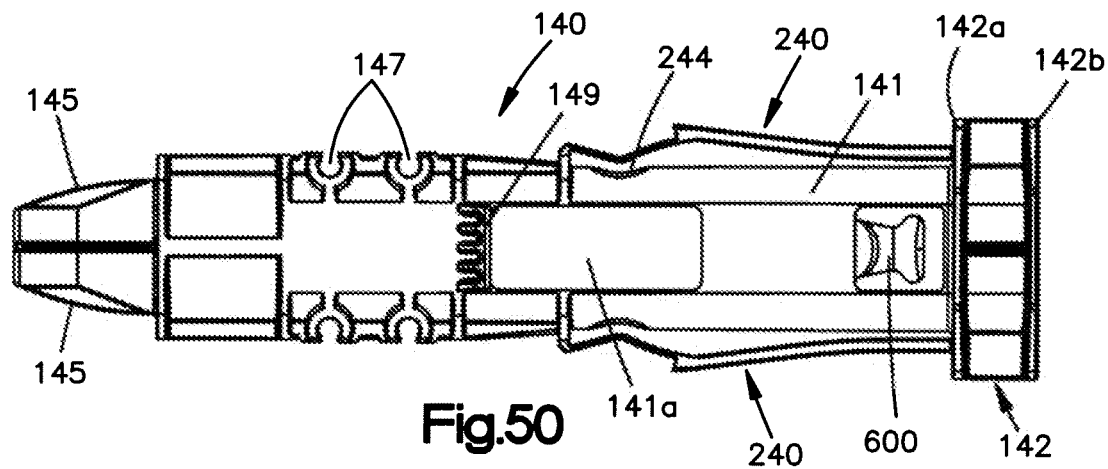
FIG. 50 is a side view of the cartridge container.
Figure 51:
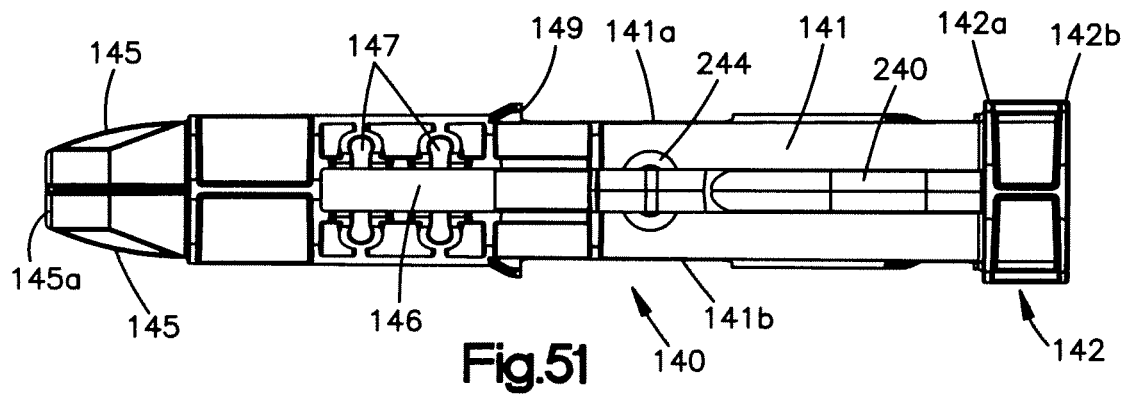
FIG. 51 is another side view of the cartridge container of FIG. 51 rotated 90° about an axis.
Figure 58:
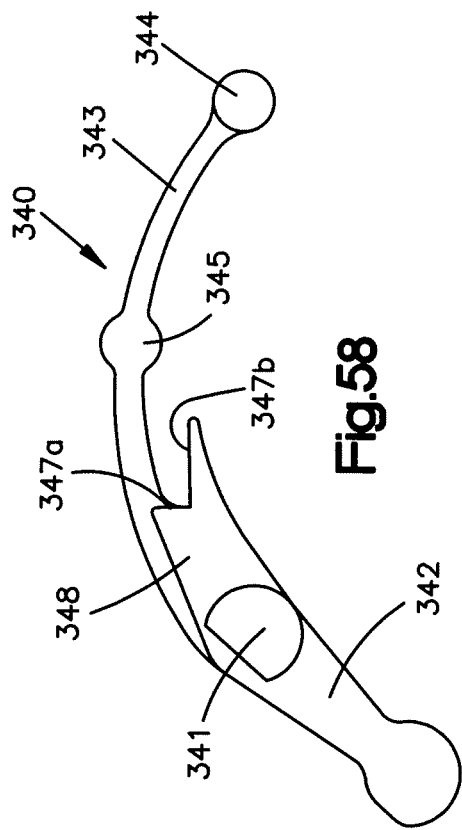
FIG. 58 is a side view of the locking tooth.

An elongated slot 146 is formed on each side of the elongated body 141. The slot 146 extends from the ends of the strut 242, as shown in FIGS. 49 and 51. Each slot 146 is sized to receive a locking tooth 340. As shown in FIGS. 1, 2, 4, 5, 7, 9, 16, 39 and 41, the locking teeth 340 are locked on opposing sides of the cartridge container 140. The locking teeth 340 are provided to hold back the needle cover 150 from deploying until after operation of the auto-injector 100. A pair of locking teeth 340 are provided. While not preferred, it is contemplated that a single locking tooth 340 can be employed.

Each locking tooth 340 is capable of pivoting about the bearing axle 341 within the axle slot 147. Multiple axle slots may be provided such that the position of the tooth 340 may be adjusted. As shown in FIGS. 56-59, each locking tooth 340 has a tab 342 having a bearing surface 342a. The tab 342 is positioned within the slot 146 such that it extends into the interior of the elongated body 141 and is capable of contacting the cartridge 160. As the cartridge 160 is advanced within the body 141 during operation of the auto-injector 100, the contact between the cartridge 160 and the bearing surface 342a causes the locking tooth 340 to rotate about the axle 341. While the surface 342a contacts the cartridge 160, the locking teeth 340 have minimal or negligible impact on the movement of the cartridge 160 within the container 140 during the injection operation. The low or minimal force applied by the locking teeth to the cartridge is advantageous in that it does not build pressure within the cartridge that could prematurely burst the diaphragm before the needle is fully extended. Furthermore, the movement of the cartridge 160 within the container 140 is not impeded or negligibly impeded by the locking teeth 340. The tab 342 extends from one side of the axle 341. A spring tail 343 extends from an opposing side of the axle 341. The spring tail 343 is positioned within the slot 146 and is designed to slide along the cartridge container 140. The spring tail 343 serves to bias the locking tooth 340 into a locked position such that the needle cover 150 is retained or locked in a retracted position prior to operation of the auto-injector 100. It is contemplated that the spring tail 343 may be replaced with a spring assembly. A bearing surface 344 is provided on one end of the tail 343 to permit the spring tail 343 to slide smoothly along the cartridge container 140 within slot 146. The bearing surface 344 and central body 345 provide a flat area for an ejector pin.

Formed below the spring tail 343 is a v-shaped notch 347. The notch 347 has a locking surface 347a on one side which holds the needle cover 150 before activation of the auto-injector 100. Another surface 347b limits the travel of the tooth 340 within the cartridge container 140 to limit its rotation. The notch 347 is formed as part of a tab 348, which extends on either side of the spring tail 343. The locking teeth 340 increase the flexibility of the auto-injector 100. Numerous cartridges of various lengths and diameters can be used without modifying the auto-injector 100. The spring action of the tails 343 adjust the position of the locking teeth 340 such that the surface 342a contacts the cartridge 160.

The cartridge container 140 further includes a pair of openings 141a and 141b, which are formed on opposing sides of the body 141. The openings 141a and 141b permit viewing of the contents of the cartridge 160 such that the user can visually inspect the medicament prior to operation of the auto-injector 100. Prior to use the openings 141a and 141b are aligned with corresponding openings in the needle cover 150 such that the user can view the contents of cartridge 160 through the outer body 110. A ledge 149 having a plurality of reinforcing ribs 149a is formed adjacent one end of the opening 141. The ledge 149 contacts the edge 154a of the opening 154 in the needle cover 150 to prevent the needle cover 150 from moving any further forward relative to the cartridge container 140 so that the needle cover 150 cannot be pulled out of the outer body 110. When in this position, the locking surface 243 of the locking wings 240 engages the end of needle cover 150 to prevent the needle cover 150 from being inserted back into the outer body 110. When the ledge 149 is in contact with the edge of the opening in the needle cover 150, the openings in the cartridge container and the needle cover are no longer aligned such that the user cannot view the cartridge 160 through the outer body 110. This provides a visual guide indicator to the user that the auto-injector 100 has been used.

The needle cover 150 will now be described in greater detail in connection with FIGS. 12-15,38,42,43 and 53-54. The needle cover 150 has a generally elongated hollow body 151 having a shape that is complementary to the shape of outer body 110. The elongated body 151 is slidably received within the outer body 100. One end of the hollow body 151 is tapered having an enclosed end surface 152. The end surface 152 has an opening 152a sized to permit the passage of the needle of the cartridge 160 there through during an injection operation, as shown in FIGS. 7 and 8. The end surface 152 is intended to be placed on the injection surface of the user during operation of the auto-injector 100 A needle cover spring 153 is compressed between the end surface 152 of the needle cover 150 and the cartridge container 140, as shown in FIGS. 1, 2, 4, 5, 7, and 9. The auto-injector 100 with needle cover 150 in accordance with the present invention is designed to function like auto-injectors without needle covers in that a similar activation force is required to operate the auto-injector. As such, the spring 153 has a very low load. The biasing force for the cover 150 is less than the activating force of the auto-injector 100. The maximum load for the spring 153 is preferably 1.5 pounds. The load is lower than the activation force (1.5 versus 4-8) necessary to actuate the auto-injector 100 such that the needle cover 150 does not impact the operation of the auto-injector 100 when compared to injectors without covers such as disclosed in the '893 patent. The ribs 145 on the cartridge container 140 act to stabilize the spring 153 within the cover 150. The hollow body 151 may include indents 151a, shown in FIGS. 53 and 54. The indents 151a reduce the thickness of the plastic to conserve materials.

The hollow body 151 further includes a pair of openings 154 formed thereon. As discusses above, the openings 154 align with the openings 141a and 141b in the cartridge container 140 prior to activation to allow visibility of the medicament within the cartridge 160. Edge surface 154a of the opening 154 is designed to contact ledge 149 to prohibit further advancement of the needle cover 150.

Slots 155 are provided on opposing sides of the needle cover 150. The slots 155 are positioned to be aligned with the locking wings 240 and the locking teeth 340. The slots 155 guide and support the locking wings 240 prior to deployment of the needle cover 150. A cross slot 155a may be provided to aid in the assembly of the auto-injector 100 such that the locking teeth 340 can be inserted in place on the cartridge container 140 through slot 155 in the needle cover 150. Bearing surface 344 can be placed through the slot 155a. Locking projections 156 extend inwardly into the slot 155. The locking projections 156 are configured to engage the locking surface 347a on the locking teeth 340. Multiple projections 156 are provided to correspond to the multiple axle slots 147 in the cartridge container 140 for the bearing axle 341.

An interior groove 157 is provided within the interior of the hollow body 151. The interior groove 157 is axially aligned with the slots 155. A portion of the strut 241 is aligned in the groove 157 when the cover member 150 is in the position shown in FIGS. 12 and 13. The grooves are aligned with the locking wings 240 to provide support and prevent sideways collapsing of the locking wings 240.

The cartridge 160 includes a generally elongated glass tube having an opening 161 at one end sized to receive the plunger 438 and collet 430. The flange 436 on the collet 430 is designed to contact the end of the cartridge 160 to limit the inward travel of the plunger and collet into the cartridge 160 to control the dosage dispensed through the needle 162. The needle 162 is attached to a hub assembly 163 which is secured to another end of the cartridge 160. The hub assembly 163 may include a diaphragm 164 to prevent the passage of liquid medicament through the needle 162 prior to activation of the auto-injector. The needle 162 is encased in a protective sheath 165. The sheath 165 is secured to the hub assembly 163. The needle 162 pierces the sheath 165 during operation, when the needle 162 projects through the needle cover 150. The cartridge 160, as illustrated, provides a container for a dose of liquid medicament. It is not intended that the auto-injector 100 be limited solely to the use of a single liquid, rather, it is contemplated that one or more liquids may be stored in cartridge 160 that mix upon activation of the auto-injector 100. Furthermore, a solid medicament and a liquid can be separately stored in the cartridge 160 whereby the solid is dissolved in the liquid prior to dispensing.

The operation of the auto-injector 100 will now be described in greater detail. The auto-injector 100 is shown in an unactivated state in FIGS. 1, 2 and 3. The release pin 120 is secured in place such that the pin 125 is received within the hole 234 and the hole 435a in the collet 430 such that the side arms 433 can not be inwardly deflected. In this position, the needle cover 150 is held in a locked retracted position by the locking teeth 340. The locking surfaces 347a are biased by the spring tails 343 into alignment with the locking projections 156 on the needle cover member 150. In this position, the auto-injector 100 cannot be operated and the needle 162 is not exposed.

Figure 4:
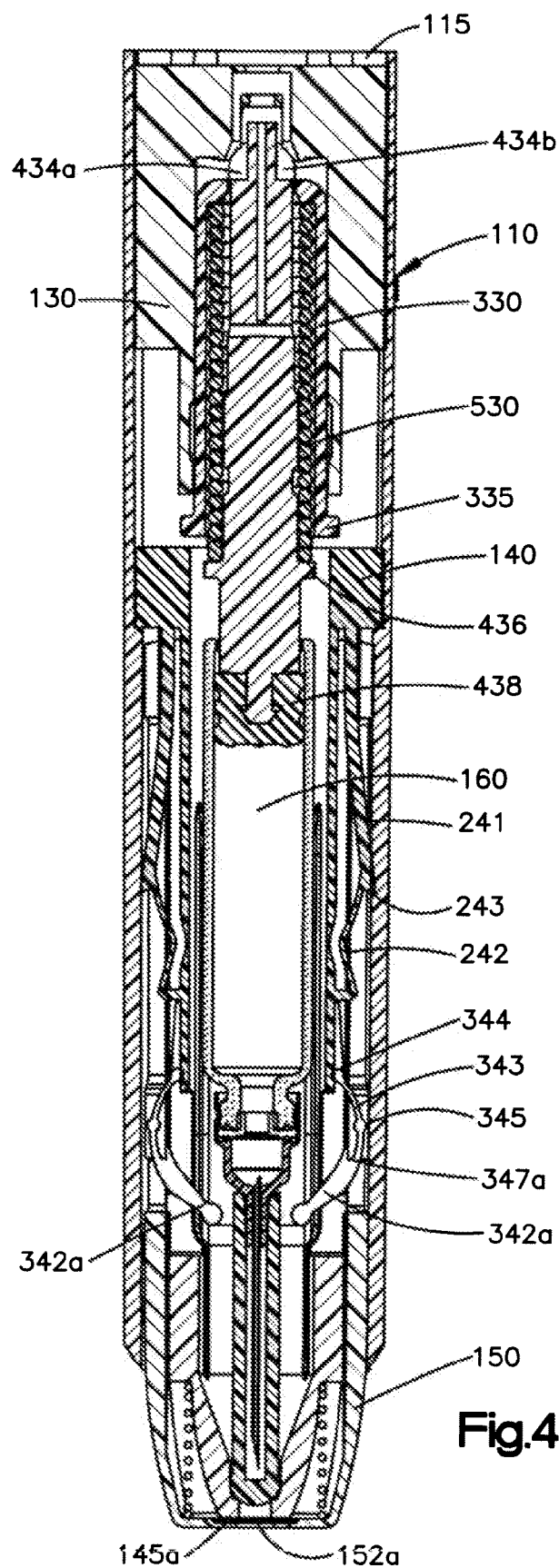
FIG. 4 is a side cross sectional view of the auto-injector of FIG. 1 having the release pin removed in preparation for activation.

When operation of the auto-injector 100 is desired, the release pin 120 is grasped by the peripheral ledge 124 and pulled to remove the release pin 120 from the end of the auto-injector 100. This readies the auto-injector 100 for operation, as shown in FIG. 4. The arrowheads 434a and 434b and side arms 433a and 433b are now capable of being compressed together when the auto-injector 100 is activated. The locking wings 240 are not compressed or stressed at this time.

As shown in FIGS. 5 and 6, the user presses the end surface 152 of the needle cover 150 against the injection site. This causes the pre-compressed spring 153 to be slightly further compressed until the needle cover 150 moves and contacts the front end 145a of the cartridge container 140 (see FIG. 51), thus moving the ledge 142 of the cartridge container 140 rearwardly. The force of spring 153 is less that the force of spring 530. The needle cover 150, the cartridge container 140 and the cartridge 160 are then moved rearwardly into the outer body 110. The cartridge container 140 moves upward into the outer body 110 until the ledge 142 thereof contacts the ledge 335 of the power pack inner body 330. The power pack inner body 330, and the collet 430 and the spring assembly 530 are then pushed rearwardly into the auto-injector 100 into the power pack outer body 230. The collet 430 moves upwardly until it contacts the collet activation structure 239, shown in FIG. 28. The arrowheads 434a and 434b contact the sloped activation surface 239a. The arrowheads 434a and 434b are compressed together by the sloped surface 239 as the collet 430 moves rearwardly, such that the arrowheads 434a and 434b are released from the collet retention surface 332b. During this loading operation, the needle cover 150 is rearwardly pushed a small amount into outer body 110. When this occurs, the preload on the locking teeth 340 provided by the spring 153 is temporarily removed. As such, the v-shaped notch 347 temporarily disengages projection 156 formed on the needle cover 150. During this operation, the projection 156 no longer contacts either surface 347*a* or 347*b*, but remains in a space provided between the surfaces. As such, when pressure from the needle cover 150 is removed, the projection 156 will return into contact with the surfaces 347*a* or 347*b*. The locking teeth 340 will completely release the needle cover 150 only in response to movement of the cartridge 160 as it travels forwardly within the cartridge container 140. Accordingly, the needle cover 150 cannot deploy until the cartridge 160 moves.

The spring 530 and collet 430 simultaneously force the cartridge 160 and the cartridge container 140 forward toward the open front end of the outer body 110. Once the needle 162 has been extended through the needle cover 150, pressure of the medicament within the cartridge 160 causes the diaphragm 164 to burst permitting the flow of medicament into the user. The drug is forced through the needle 162 allowing the plunger 438 and collet 430 to move further into the cartridge 160. The cartridge container 140 retains the sheath 165 and also prevents the spring force of the spring 530 from being transferred through the cartridge 140 onto the needle cover 150 and the injection site. That is, the force from spring 530 that drives the cartridge 160 forward is opposed by the front end of the cartridge container 140, with the sheath 165 compressed there between, rather than force being received directly by the needle cover 150. In addition, the needle cover spring force is less than the activation force required to collapse the collet to release the collet during actuation. Preferably, the needle cover spring force is about 0.25 to 0.75 of the minimum activation force. The power pack residual spring force after activation is contained within the cartridge container 140, cartridge 160, the outer body 110 and the power pack outer body 230. This arrangement advantageously prevents a kickback effect from occurring. As such, the auto-injector is not pushed away from the injection site during activation to ensure that the proper dose of medicament is administered and the proper needle extended length or proper needle penetration is maintained. This effect would occur if the spring force from the spring 530 were transferred to the needle cover 150 and the injection site, whereby the auto-injector 100 could be pushed away from the injection site and alter the location of the needle 162 within the injection site. This has several negative impacts including startling the patient; changing the injection from an intramuscular to subcutaneous injection, which will affect pk levels. At the same time, the cartridge 160 is advanced within cartridge container 140 (i.e., when the needle 160 goes from a retracted position to extended position). The advancement of the cartridge 160 causes the locking tooth 340 to pivot about the axle 341. This is in response to cartridge 160 contacting bearing surface 342*a* and pushing the bearing surface 342*a* away from the main longitudinal axis of the needle 162. This rotation of the locking tooth 340 causes the locking surface 347*a* to disengage the locking projections 156. The surface 347*b* limits the rotation of the locking tooth 340. At this point, the cover member 150 is in an unlocked position such that it can move with respect to the cartridge container 140. The release of the collet 430 from the collet retention surface 332*b* forces the end of the power pack inner body 330 into contact with the power pack outer body 230.

Figure 11:
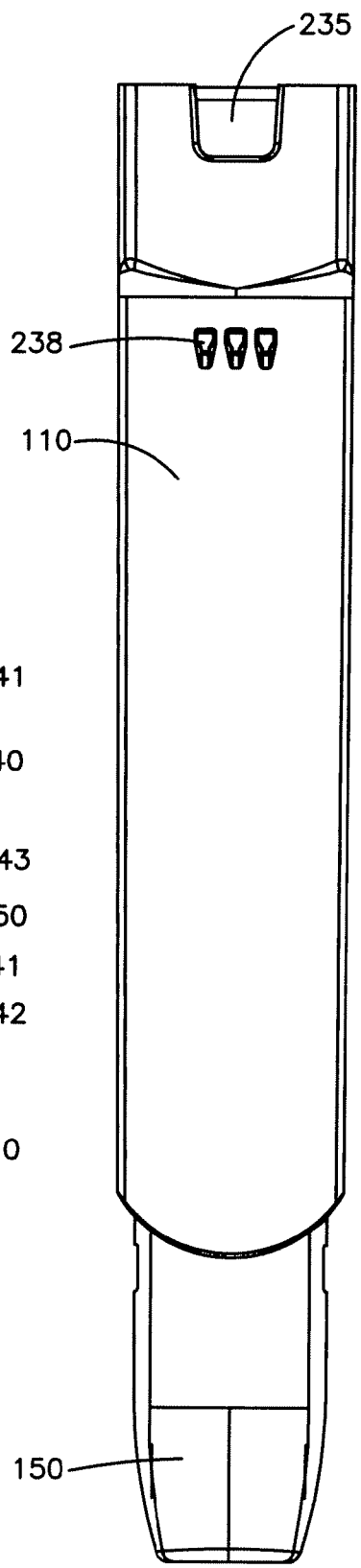
FIG. 11 is a side schematic view of the auto-injector of FIG. 9.
Figure 16:
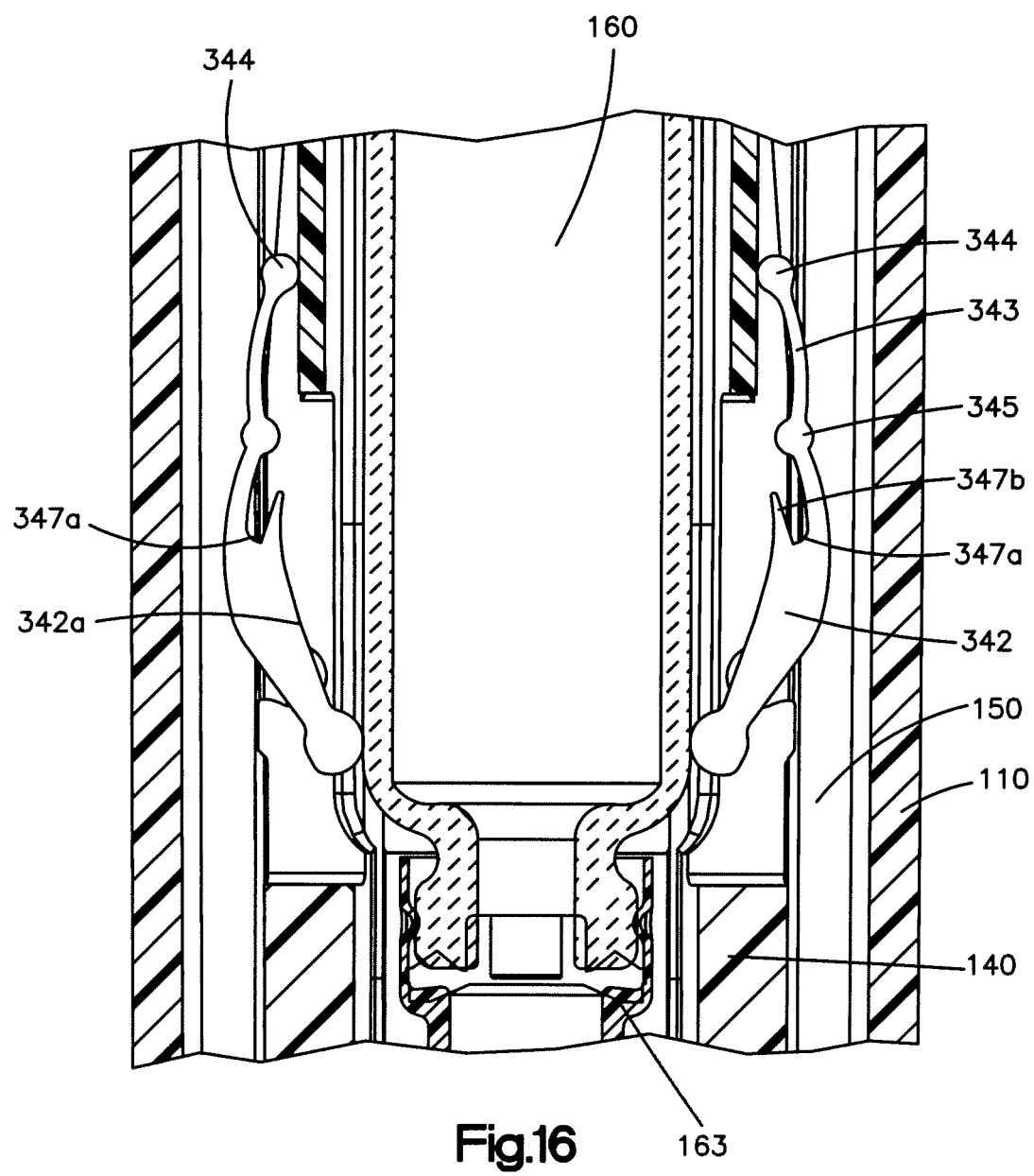
FIG. 16 is an enlarged cross sectional view illustrating the position of the locking teeth when the needle cover is in the extended protective position.
Figure 23:
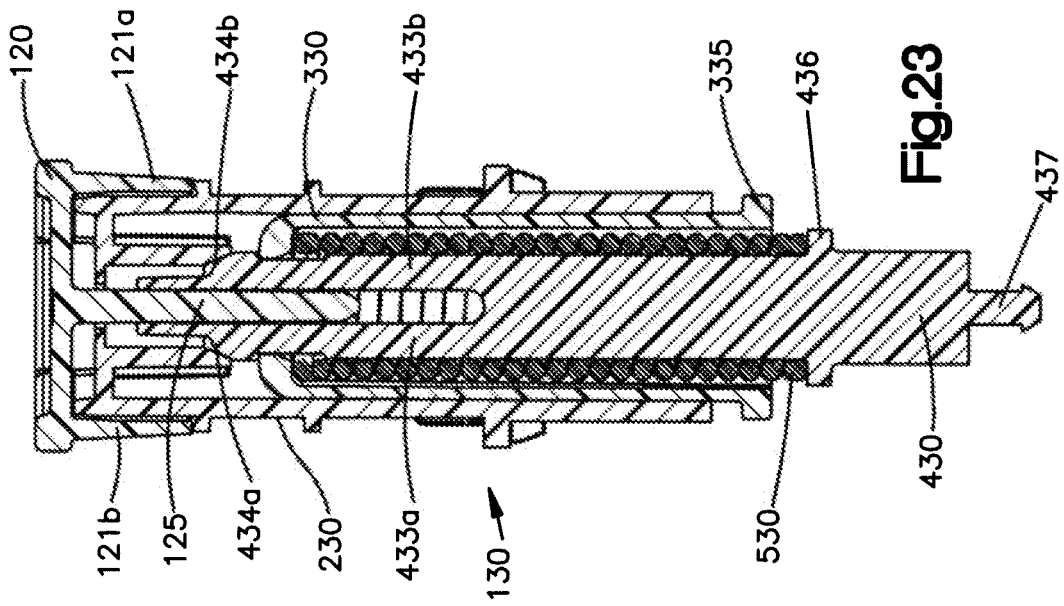
FIG. 23 is a side cross sectional view of the power pack of FIG. 22.
Figure 22:
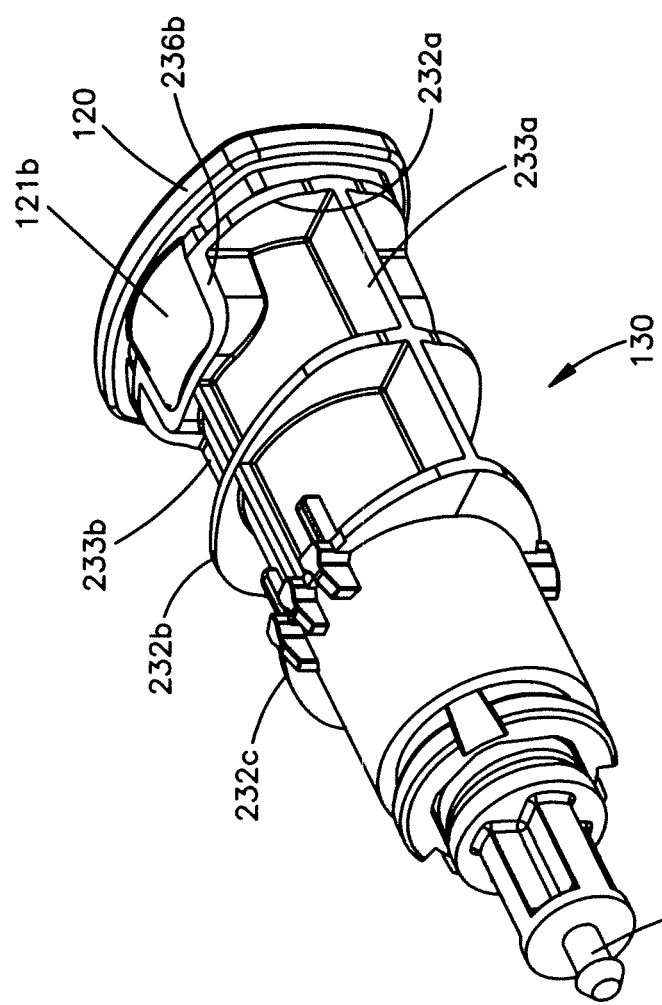
FIG. 22 is a right bottom perspective view of the power pack of the auto-injector in an assembled state.

Once the dose has been injected into the user, the user removes the auto-injector 100 from the injection surface. Since the needle cover 150 is not locked with respect to the cartridge container 140, the spring 153 forces the needle cover 150 out of the outer body 110 to cover the exposed needle 162, as shown in FIGS. 9 and 11. Since the slot 155 is aligned with groove 157 and a portion of the strut 241 is retained in the slot 157, the portion of the strut 241 moves into the groove 157 when the cover 150 moves outwardly. As the needle cover 150 slides outwardly, the locking wings 240 are temporarily compressed by the needle cover 150 as the thicker strut 241 slides through the groove 157. This compression occurs when the bottom surface of the groove 157 contacts the top surface of the strut 241. The wings 240 compress in the manner shown in the dashed lines in FIG. 52. Once the thicker strut 241 clears the groove 157 such that the wings 240 and needle cover 150 are in the position illustrated in FIGS. 10, 14 and 15, the locking surface 243 contacts the end of the needle cover 150 to prevent the needle cover from being reinserted into outer body 110. In the event that inward force is applied, the struts 241 and 242 compress such that the locking wing 240 is pressed against the body 141 of the cartridge container 140 such that the surface 243 remains engaged with the needle cover 150. This arrangement limits the inward travel of the needle cover 150. The ledge 149 engages the edge 154*a* of the opening 154 in the needle cover 150. The auto-injector 100 is now in an inoperable stored position.

The invention having been disclosed in connection with the foregoing embodiment and examples, additional variations will now be apparent to persons skilled in the art. Various modifications and variations to the above described auto-injector can be made without departing from the scope of the invention. The invention is not intended to be limited to the embodiment specifically mentioned and accordingly reference should be made to the appended claims rather than the foregoing discussion of preferred embodiments and examples to assess the spirit and scope of the invention in which exclusive rights are claimed.

We claim:
1. An automatic injector comprising:
a housing;
a cartridge container disposed within the housing;
a cartridge received in the cartridge container, the cartridge containing a medicament and including a needle assembly to allow the medicament to be dispensed there through, the needle assembly comprising a needle;
an actuation assembly disposed within the housing and having a stored energy source, the actuation assembly operative to drive the medicament through the needle during a medicament dispensing operation in response to release of stored energy from the stored energy source; and
a needle cover received in the housing, the needle cover having an opening operative to receive there through at least part of the cartridge container, the needle cover having a locked retracted position with respect to the housing prior to a medicament dispensing operation, the needle cover having a surface operative to contact an injection site prior to a medicament dispensing operation.

2. The automatic injector of claim 1 further comprising a locking mechanism operative to prevent movement of the needle cover outward from the housing when the needle cover is in the locked retracted position, the locking mechanism comprising a locking tooth that engages the needle cover when the needle cover is in the locked retracted position.

3. The automatic injector of claim 2 wherein the locking tooth has a spring action extension that adjusts the position of the locking tooth with respect to the cartridge to accommodate cartridges of different sizes and needles of different sizes received in the cartridge container.

4. The automatic injector of claim 1 further comprising a locking mechanism operative to prevent movement of the needle cover outward from the housing when the needle cover is in the locked retracted position, the locking mechanism disposed within the housing to protect against tampering and dirt ingress via external contact of the automatic injector.

5. The automatic injector of claim 1 wherein the needle cover has a locked extended position with respect to the housing after the medicament dispensing operation.

6. The automatic injector of claim 5 further comprising a locking mechanism operative to prevent movement of the needle cover into the housing when the needle cover is in the locked extended position, the locking mechanism comprising a locking arm connected to the cartridge container that engages an outer edge of the needle cover when the needle cover is in the locked extended position.

7. The automatic injector of claim 6 wherein the locking arm has a thick strut portion and a thin strut portion, the thick strut portion outwardly curved and the thin strut portion inwardly curved.

8. The automatic injector of claim 1 wherein the needle cover surface operative to contact an injection site is an enclosed front end surface of the needle cover, the front end surface having an opening sized to permit passage of only the needle there through.

9. The automatic injector of claim 1 wherein the needle cover surface operative to contact an injection site causes the automatic injector to initiate a medicament dispensing operation when the needle cover surface is pressed with sufficient force against an injection site.

10. The automatic injector of claim 1 wherein the needle cover extends beyond the housing in the locked retracted position.

11. The automatic injector of claim 1 wherein the needle cover is received in the housing between the housing and the cartridge container.

12. The automatic injector of claim 1 wherein no part of the housing is operative to contact an injection site during a medicament dispensing operation.

13. The automatic injector of claim 1 wherein the housing has an oval-shaped lateral cross section.

14. The automatic injector of claim 1 further comprising a non-removable needle sheath disposed about the needle.

15. The automatic injector of claim 1 further comprising a plunger rearwardly confining the medicament through an opening in the cartridge, the actuation assembly comprising a one-piece molded collet coupled to the plunger, the collet driving the plunger farther into the cartridge during a medicament dispensing operation.

16. The automatic injector of claim 1 wherein stored energy released from the stored energy source during a medicament dispensing operation is not transferred to the needle cover.

17. The automatic injector of claim 1 wherein residual stored energy released from the stored energy source is contained by the cartridge container, the cartridge, the housing, and the actuation assembly to prevent kickback of the automatic injector during a medicament dispensing operation.

18. The automatic injector of claim 1 further comprising a needle cover spring positioned inside the needle cover between an end surface of the needle cover and a front end of the cartridge container.

19. The automatic injector of claim 1 wherein the cartridge container has a closed front end having an opening therein sized to receive only the needle there through during a medicament dispensing operation.

20. The automatic injector of claim 1 wherein the cartridge container has multiple axle slots, each slot operative to receive and rotatably support a locking tooth, wherein the position of the locking tooth in one of the axle slots on the cartridge container is adjustable such that needles of varying lengths and cartridges of varying lengths and diameters can be accommodated within the cartridge container.

21. The automatic injector of claim 1 wherein the medicament comprises epinephrine or diazepam.

22. A needle cover for an automatic injector comprising: an elongated hollow body having an enclosed end surface at one end, the enclosed end surface having an opening sized to permit passage of only a needle of a cartridge, the hollow body having a pair of slots extending longitudinally on opposite sides of the hollow body, the hollow body having a plurality of locking projections extending inwardly into each of the slots.

23. The needle cover of claim 22 wherein the hollow body further has a pair of openings on opposite sides of the hollow body, the hollow body having a pair of laterally extending edge surfaces along each of the openings.

24. The needle cover of claim 22 wherein the hollow body further has a pair of grooves extending inside the hollow body in alignment with the pair of slots.

25. The needle cover of claim 22 wherein the hollow body further has a pair of cross slots, each cross slot extending across one of the pair of slots.

\* \* \* \* \*